US008892432B2

(12) United States Patent
Shimada et al.

(10) Patent No.: US 8,892,432 B2
(45) Date of Patent: Nov. 18, 2014

(54) SIGNAL PROCESSING SYSTEM, APPARATUS AND METHOD USED ON THE SYSTEM, AND PROGRAM THEREOF

(75) Inventors: Osamu Shimada, Tokyo (JP); Akihiko Sugiyama, Tokyo (JP)

(73) Assignee: NEC Corporation, Tokyo (JP)

( * ) Notice: Subject to any disclaimer, the term of this patent is extended or adjusted under 35 U.S.C. 154(b) by 519 days.

(21) Appl. No.: 12/738,442

(22) PCT Filed: Oct. 15, 2008

(86) PCT No.: PCT/JP2008/068646

§ 371 (c)(1), (2), (4) Date: Apr. 16, 2010

(87) PCT Pub. No.: WO2009/051132

PCT Pub. Date: Apr. 23, 2009

(65) Prior Publication Data

US 2010/0217586 A1 Aug. 26, 2010

(30) Foreign Application Priority Data

Oct. 19, 2007 (JP) ................................ 2007-271963

(51) Int. Cl.

| | |
|---|---|
| ***G10L 21/00*** | (2013.01) |
| ***G10L 21/0272*** | (2013.01) |
| *G05B 15/00* | (2006.01) |
| *G01N 33/50* | (2006.01) |
| *H04B 1/10* | (2006.01) |
| *H04N 7/14* | (2006.01) |
| *H04R 5/00* | (2006.01) |
| *H04R 1/40* | (2006.01) |
| *H04R 5/02* | (2006.01) |
| *H04R 9/08* | (2006.01) |

(52) U.S. Cl.

CPC ................................ *G10L 21/0272* (2013.01)
USPC ................. 704/226; 381/20; 381/97; 381/18; 381/356; 381/309; 700/258; 702/19; 375/350; 348/14.01

(58) Field of Classification Search

USPC ........ 704/226; 381/17, 20, 97, 18, 94.3, 94.1, 381/23.1, 310, 356, 111, 119, 312, 92, 309; 700/258; 375/350; 702/19
See application file for complete search history.

(56) References Cited

U.S. PATENT DOCUMENTS 5,761,315 A * 6/1998 Iida et al. ........................ 381/18
5,862,240 A * 1/1999 Ohkubo et al. ............... 381/356

(Continued)

FOREIGN PATENT DOCUMENTS

JM 2007-067858 A 3/2007
JP 2-59000 A 2/1990

(Continued)

OTHER PUBLICATIONS

Asakura Publishing Co., Ltd., Mechanism of Calculation by Brain—Dynamics in Bottom-up/Top-down, 2005, pp. 203-216 Trans Partial of pp. 214-215.

(Continued)

*Primary Examiner* — Paras D Shah
*Assistant Examiner* — Neeraj Sharma
(74) *Attorney, Agent, or Firm* — Foley & Lardner LLP

(57) ABSTRACT

Provided is a signal separation system including a rendering unit which receives a first and a second input signal and positions the first input signal according to rendering information.

5 Claims, 16 Drawing Sheets

(56) References Cited

U.S. PATENT DOCUMENTS

| | | | | |
|---|---|---|---|---|
| 6,697,491 | B1 * | 2/2004 | Griesinger | 381/20 |
| 7,174,023 | B2 * | 2/2007 | Ozawa | 381/94.1 |
| 7,242,782 | B1 * | 7/2007 | Kasai et al. | 381/97 |
| 7,254,241 | B2 * | 8/2007 | Rui et al. | 381/92 |
| 7,330,556 | B2 * | 2/2008 | Kates | 381/312 |
| 7,336,792 | B2 * | 2/2008 | Sasaki | 381/17 |
| 7,590,528 | B2 | 9/2009 | Kato et al. | |
| 8,090,111 | B2 * | 1/2012 | Aichner et al. | 381/56 |
| 8,184,814 | B2 * | 5/2012 | Cvetkovic | 381/26 |
| 8,229,740 | B2 * | 7/2012 | Nordholm et al. | 704/226 |
| 8,233,642 | B2 * | 7/2012 | Mao | 381/122 |
| 8,271,200 | B2 * | 9/2012 | Sieracki | 702/19 |
| 8,340,317 | B2 * | 12/2012 | Pfaffinger et al. | 381/93 |
| 8,351,554 | B2 * | 1/2013 | Grbic et al. | 375/350 |
| 8,483,413 | B2 * | 7/2013 | Hartung et al. | 381/302 |
| 8,755,547 | B2 * | 6/2014 | Mejia et al. | 381/320 |
| 2004/0072336 | A1 * | 4/2004 | Parra et al. | 435/287.2 |
| 2005/0143989 | A1 * | 6/2005 | Jelinek | 704/226 |
| 2005/0190936 | A1 * | 9/2005 | Miura et al. | 381/309 |
| 2008/0056517 | A1 * | 3/2008 | Algazi et al. | 381/310 |
| 2008/0130918 | A1 * | 6/2008 | Kimijima | 381/107 |
| 2008/0273722 | A1 * | 11/2008 | Aylward et al. | 381/302 |
| 2009/0030552 | A1 * | 1/2009 | Nakadai et al. | 700/258 |
| 2009/0034756 | A1 * | 2/2009 | Volker et al. | 381/119 |
| 2009/0052703 | A1 * | 2/2009 | Hammershoi | 381/310 |
| 2010/0002886 | A1 * | 1/2010 | Doclo et al. | 381/23.1 |

FOREIGN PATENT DOCUMENTS

| | | | |
|---|---|---|---|
| JP | 3-126398 | A | 5/1991 |
| JP | 5-60100 | U | 8/1993 |
| JP | 8-561698 | A | 2/1996 |
| JP | 11-46400 | A | 2/1999 |
| JP | 2002-78100 | A | 3/2002 |
| JP | 2002-204175 | A | 7/2002 |
| JP | 2004-129038 | A | 4/2004 |
| WO | WO 2007-052645 | A1 | 5/2007 |

OTHER PUBLICATIONS

Bernard Widrow et al., Adaptive Noise Cancelling: Principles and Applications, Proceedings of the IEEE, Dec. 1975,, 26 pages, vol. 63, No. 12.

Shigeji Ikeda et al., An Adaptive Noise Canceller With Low Signal-Distortion in the Presence of Crosstalk, IEICE Trans. Fundamentals, Aug. 1999, pp. 1517-1525, vol. E82-A, No. 8.

ISO/IEC 23003-1, Part 1 MPEG Surround, Information Technology — MPEG Audio Technologies, 2007, 10 pages.

Darren B. Ward et al., Constant Directivity Beamforming, Microphone Arrays, Signal Processing Techniques and Applications, 2001, 8 pages, Springer.

Swen Nordholm et al., Adaptive Microphone Array Employing Spatial Quadratic Soft Constraints and Spectral Shaping, Speech Enhancement, Signals and Communication Technology, 2005, pp. 229-246, Springer.

Yiteng Huang et al., Separation and Dereverberation of Speech Signals With Multiple Microphones, Speech Enhancement, Signals and Communication Technology, 2005, pp. 271-369.

N.S. Jayant et al., Digital Coding of Waveforms, Principles and Applications to Speech and Video 1990, pp. 510-563, Prentice-Hall.

Alan V. Oppenheim et al., Digital Signal Processing, 1995, pp. 238-251, Prentice-Hall.

P. P. Vaidyanathan, Multirate Systems and Filter Banks, 1993, pp. 188, 271, Prentice-Hall.

Tomoya Takatani et al., High-Fidelity Blink Source Separation Using SIMO-Model-Based ICA, Technical Report of IEICE, Jan. 20, 2003,pp. 19-24.

Japanese Office Action.2009-538109, Dec. 12, 2013, 6 pages.

* cited by examiner

RENDERING SELECTION INFORMATION

RENDERING INFORMATION

FIG. 17
MICROPHONE $6_1$
MICROPHONE $6_0$

SIGNAL PROCESSING SYSTEM, APPARATUS AND METHOD USED ON THE SYSTEM, AND PROGRAM THEREOF

TECHNICAL FIELD

The present invention relates to a signal processing system, a signal processing apparatus, a signal processing method, and a signal processing program for separating an input signal containing a plurality of signal components.

BACKGROUND ART

Demands for separating and extracting a specific signal component from a given input signal having a plurality of mixed signal components are encountered in a variety of scenes in daily life. An example of such scenes is recognition of conversation or desired voice in a noisy environment. In such a scene, conversation and/or desired voice are generally captured using an electroacoustic transducer element, such as a microphone, at a point in space. The captured conversation and/or desired voice are converted into an electric signal, and manipulated as an input signal.

One conventionally known system applied to an input signal containing a plurality of signal components comprising desired voice and background noise is a noise suppression system (which will be referred to as a noise suppressor hereinbelow), which enhances the desired voice by suppressing the background noise. The noise suppressor is a system for suppressing noise superposed over a desired acoustic signal. In general, the noise suppressor uses an input signal transformed into a frequency domain to estimate a power spectrum of a noise component, and subtracts the estimated power spectrum of the noise component from the input signal. Alternatively, there is a widespread method including multiplying the input signal by a gain less than one to obtain a result equivalent to that by subtraction. Noise mixed into a desired acoustic signal is thus suppressed. Moreover, such a noise suppressor may be applied to suppression of non-stationary noise by continuously estimating the power spectrum of noise components. A technique related to such a noise suppressor is disclosed in Patent Document 1, for example (which will be referred to as first related technique).

Generally, the noise suppressor, which is the first related technique, has a tradeoff between residual noise left from suppression, i.e., a degree of separation of desired voice from background noise, and distortion involved in enhanced output voice. A higher degree of separation to reduce residual noise results in increased distortion, while reduced distortion causes the degree of separation to decrease and residual noise to increase. Particularly, for a smaller power ratio of desired voice to noise, distortion contained in an output obtained by a least noise suppression effect is more significant.

On the other hand, the fact that a human auditory organ has ability to discriminating differently localized signals is disclosed in Non-patent Document 1. Perception of localization requires multi-channel signals. Therefore, in a case that a monophonic signal is input, it must be converted into a multi-channel signal. One method of controlling signal localization is rendering processing for manipulating the amplitude and phase of a given signal. A technique related to the rendering processing is disclosed in Patent Document 2. In a case that at least two channels of signals are input, the human auditory organ uses the difference in amplitude and phase (a relative delay at a reception point) between these signals to spatially localize these signals. Based on this principle, rendering controls a localized position by manipulating the amplitude and phase of an input signal. For example, there is a rendering system for convoluting an unlocalizable monophonic signal with a plurality of transfer functions defined by the amplitude and phase having a specific relationship to generate a multi-channel output. Such a rendering system is shown in FIG. 20 (which will be referred to as second related technique).

As shown in FIG. 20, a rendering system according to the second related technique receives monophonic input 0 at a rendering section 9, and outputs $M_o$-channel signals including output 0-output $M_o-1$. The rendering section 9 applies rendering to input 0 based on rendering information, and outputs a result as output 0-output $M_o-1$. In a case that input 0 contains a plurality of signal components, all the signal components are localized at the same point in space, because the same rendering processing is applied to all signal components.

Patent Document 1: JP-P2002-204175A

Patent Document 2: JP-P1999-46400A

Non-patent Document 1: "Mechanism of Calculation by Brain—Dynamics in Bottom-up/Top-down—," Asakura Publishing Co., Ltd. (2005), Pages 203-216

DISCLOSURE OF THE INVENTION

Problems to be Solved by the Invention

In the first related technique described above, residual noise, i.e., the degree of separation between desired voice and background noise, has a tradeoff with distortion contained in a signal. This poses a problem that a higher degree of separation results in significant distortion contained in separated signals. The second related technique described above also poses a problem that it provides no signal separation effect because all signal components are localized at the same point in space. In a case that a plurality of signals localized at different points in space are present, the human auditory organ is intrinsically capable of discriminating these signals. Since in the second related technique, all signal components are localized in the same point in space, such ability of separation by the human auditory organ cannot be used.

An object of the present invention is to provide a signal processing system capable of imparting different localization to a plurality of input signals to achieve a higher degree of signal separation and lower distortion for signals.

Means for Solving the Problems

A signal separation system in accordance with the present invention is characterized in comprising: a rendering section for receiving first and second input signals, and localizing a first input signal based on rendering information.

Effects of the Invention

According to the means described above, the signal processing system of the present invention localizes a plurality of input signals containing varying proportions of signal components at different positions in space by a multiple rendering section. This is processing for reducing distortion at the cost of reduced performance of signal separation. However, since performance of separation may be compensated by intrinsic functionality of the human auditory organ, distortion may be reduced while maintaining performance of signal separation.

[EXPLANATION OF SYMBOLS]

| | |
|---|---|
| 5 | Multiple rendering section |
| 6 | Microphone |
| 7 | Sound source |
| 10 | Obstacle |
| 11 | Pre-processing section |
| 12 | Microphone |
| 51, 52 | Rendering section |
| 53, 54, 115, 1132 | Adder |
| 55 | Separating section |
| 56, 57 | Memory |
| 110 | Signal component enhancing section |
| 111 | Fixed beamforming section |
| 112 | Adaptive blocking section |
| 113 | Multi-input canceller |
| 114 | Delay element |
| 116, 118, 126 | Adaptive filtering section |
| 117, 119, 121, 1133 | Subtractor |
| 120 | Noise suppression system |
| 1201 | Transform section |
| 1202 | Noise estimating section |
| 1203 | Suppression factor generating section |
| 1204 | Multiplier |
| 1205 | Inverse transform section |
| 1131 | Adaptive filtering section |

BEST MODES FOR CARRYING OUT THE INVENTION

Now several embodiments of a signal processing system in the present invention will be described in detail with reference to the accompanying drawings.

Figure 1:
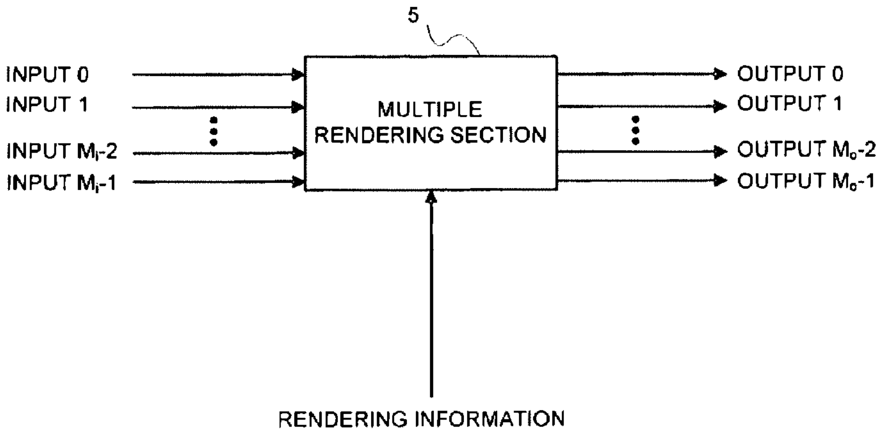
FIG. 1 A block diagram showing a first embodiment of the present invention.

A first embodiment of the signal processing system of the present invention will be described referring to FIG. 1. The signal processing system of the present invention is constructed from a multiple rendering section 5. The multiple rendering section 5 receives input 0-input $M_i-1$ as a plurality of input signals, and rendering information. The multiple rendering section 5 applies rendering to the input signals based on the rendering information, and supplies output 0-output $M_o-1$. Input 0-input $M_i-1$ are each composed of a plurality of mixed signals. The proportion of mixing of the plurality of signals contained in the input signals vary from input signal to signal. Alternatively, the plurality of signals contained in the input signals may be in the same proportion of mixing.

Now consider a case of separation of two mixed signals as an example. Consider a case in which input 0 contains a signal component 0 in a highest proportion, and input 1 contains a signal component 1 in a highest proportion. Assuming that the number of output channels is two, then, the output comprises output 0 and output 1, which are used as left and right (or right and left) channel signals. At that time, the multiple rendering section 5 applies rendering processing to input 0 and input 1 so that they are localized at different positions, and supplies output 0 and output 1. Output 0 and output 1 are transformed by an electroacoustic transducer element, such as speakers or a headphone, into acoustic signals, which are finally input to a human auditory organ for listening. Even in a case that input 0 and input 1 are signals having an insufficient degree of signal separation with reduced distortion, it can be compensated by the intrinsic function of signal separation of the human auditory organ, as discussed earlier. That is, only distortion may be reduced while maintaining performance of signal separation.

Now a description will be made on a case in which two mixed signals are a desired signal and a signal other than the desired signal, i.e., an unwanted signal. In this case, a signal in which the desired signal is dominant, i.e., the desired signal is enhanced, is input as input 0. As input I, a signal in which the unwanted signal is dominant, i.e., the unwanted signal is enhanced, is input. The rendering processing can localize input 0 to lie in the front and input 1 to lie in the rear. Such localization causes a signal in which the desired signal is dominant to be perceived as if it came from the front and a signal in which the unwanted signal is dominant to be perceived as if it came from the rear. Moreover, by localizing input 0 in the front, and localizing input 1 so that it diffusively sounds over space, a signal in which the desired signal is dominant is perceived as if it came from the front, and a signal in which the unwanted signal is dominant is perceived as if it diffusively came from the whole space. By imparting localization to input signals so that they are perceived as a point sound source and a diffused sound source, these signals are perceived as if they were separated. This is because auditory concentration can be focused more on a signal perceived as if it came from a specific point than on a signal perceived as if it diffusively came. For example, the desired signal may include voice. The unwanted signal may include noise, background noise, and signals from other sound sources.

Next, consider a more general case in which $M_i$-channel mixed signals are input, and output to $M_o$ channels. Assume that input j contains a signal component j−1 in a highest proportion. At that time, the multiple rendering section 5 applies rendering processing to input 0-input $M_{i-1}$ so that they are localized at different positions, and supplies output 0-output $M_{i-1}$. Considering input j as input of interest, rendering is applied so that input j is localized at a specific point in acoustic space, thereby generating a component corresponding to input j at output 0-output $M_{i-1}$. Similar processing is repeatedly applied to j=0–$M_{i-1}$, and a total sum of components corresponding to input 0-input $M_{i-1}$ is determined at each output to generate output 0-output $M_{i-1}$.

Subsequently, an exemplary configuration of the multiple rendering section 5 will be described in detail referring to FIG. 2. The multiple rendering section 5 is comprised of a rendering section 51, a rendering section 52, adders 53, 54, and a separating section 55. First, input 0 and input 1 are input to the rendering section 51 and rendering section 52, respectively. Moreover, rendering information is input to the separating section 55. The separating section 55 separates the rendering information into pieces of unique rendering information corresponding to the respective rendering sections, and outputs them to the corresponding rendering sections.

Rendering information is information representing a relationship between an input signal and an output signal in the rendering section 51 or 52 for each frequency component. The rendering information is represented using the signal-to-signal energy difference, time difference, correlation, and the like. An example of rendering information is disclosed in Non-patent Document 2 (ISO/IEC 23003-1:2007 Part 1 MPEG Surround).

The rendering section 51 uses a piece of unique rendering information supplied by the separating section 55 to transform input 0, and generates an output signal. The output signal corresponding to output 0 is output to the adder 53, and that corresponding to output 1 is output to the adder 54. The rendering section 52 uses another piece of unique rendering information supplied by the separating section 55 to transform input 1, and generates an output signal. The output signal corresponding to output 0 is output to the adder 53, and that corresponding to output 1 is output to the adder 54. The adder 53 adds the output signals corresponding to output 0 supplied by the rendering sections 51 and 52 to determine a sum, and outputs it as output 0. The adder 54 adds the output signals corresponding to output 1 supplied by the rendering sections 51 and 52 to determine a sum, and outputs it as output 1.

The most general unique rendering information include information on a filter, which is expressed by the filter coefficients and frequency response (amplitude and phase). In a case that the unique rendering information is given by a vector of coefficients of a finite impulse response (FIR) filter, the rendering section 51 outputs a result of convolution of input 0, input 1 and a filter coefficient h. Specifically, representing convolution of input 0 and input 1 at time k as $y_{0,k}$, $y_{1,k}$, and signal vectors at input 0 and input 1 as $x_{0,k}$, $x_{1,k}$, a relationship between the input and output can be given by the following equations:

$$y_k=h^T x_k$$

$$y_k=[y_{0,k} y_{1,k}]^T$$

$$x_k=[x_{0,k}{}^T x_{1,k}{}^T]^T$$

$$x_{0,k}=x_{1,k}=[x_k x_{k-1} \ldots x_{k-L+1}]^T$$

$$h=[h_0{}^T h_1{}^T]^T$$

$$h_0=[h_{0,k} h_{0,k-1} \ldots h_{0,k-L+1}]^T$$

$$h_1=[h_{1,k} h_{1,k-1} \ldots h_{1,k-L+1}]^T \quad \text{[Equation 1]}$$

where L denotes the number of taps in the filter. In this expression, the filter coefficient h is the unique rendering information. Specifically, in a case that out-of-head sound localization is intended, the filter coefficient is known as a head-related transfer function (HRTF). Since in the example shown in FIG. 2, the number of output channels is two, two sets $h_0$, $h_1$ of filter coefficients are input. In a case that the number of output channels is two or more, i.e., for an $M_o$-channel output, $M_o$ sets of filter coefficients are input. The operation of the rendering section 52 is identical to that of the rendering section 51 except for the input and filter coefficients. Moreover, as the number of kinds of input signals increases, the number of rendering sections and number of sets of filter coefficients increase.

In a case that the unique rendering information is given as frequency response, a product of complex numbers representing the frequency domain expression of input 0 and input 1 and the frequency response is determined to produce output 0 and output 1. At that time, time-frequency transform such as Fourier transform, and its inverse transform are applied before and after the rendering section. This calculation is represented by frequency domain expression of [Equation 1].

Subsequently, a second exemplary configuration of the multiple rendering section 5 will be described in detail referring to FIG. 3. The multiple rendering section 5 is comprised of a rendering section 51, a rendering section 52, adders 53, 54, and a memory 56. The multiple rendering section 5 in FIG. 3 has a configuration in which the separating section 55 included in FIG. 2 is substituted with the memory 56. Specifically, the rendering information is stored in the memory within the multiple rendering section, instead of being input from the outside. The multiple rendering section 5 determines localization by fixedly using the rendering information stored in the memory. Since specific rendering information stored in the memory 56 is used in the second exemplary configuration, the need of calculation involved in input and separation of rendering information is eliminated. Therefore, according to the multiple rendering section 5 in the second exemplary configuration, the volume of calculation can be reduced and the system can be simplified.

Subsequently, a third exemplary configuration of the multiple rendering section 5 will be described in detail referring to FIG. 4. The multiple rendering section 5 is comprised of a rendering section 51, a rendering section 52, adders 53, 54, and a memory 57. The multiple rendering section 5 in FIG. 4 has a configuration in which the memory 56 included in FIG. 3 is substituted with the memory 57. The memory 57 stores therein a plurality of pieces of rendering information. The memory 57 is supplied with rendering selection information for selecting from among the plurality of pieces of rendering information stored in the memory 57 for use as unique rendering information. That is, localization of an input signal is determined by selectively using an appropriate one of a plurality of pieces of rendering information stored in the memory 57, instead of using fixed rendering information. The third exemplary configuration is an intermediate version of the first and second exemplary configurations. The second exemplary configuration has a reduced volume of calculation involved in input and separation of rendering information as compared with the first exemplary configuration, and also reduces the load on a user for determining rendering information. Moreover, the third exemplary configuration has an effect that it can provide a degree of freedom for determining rendering information to a user, as compared with the second exemplary configuration.

Figure 2:
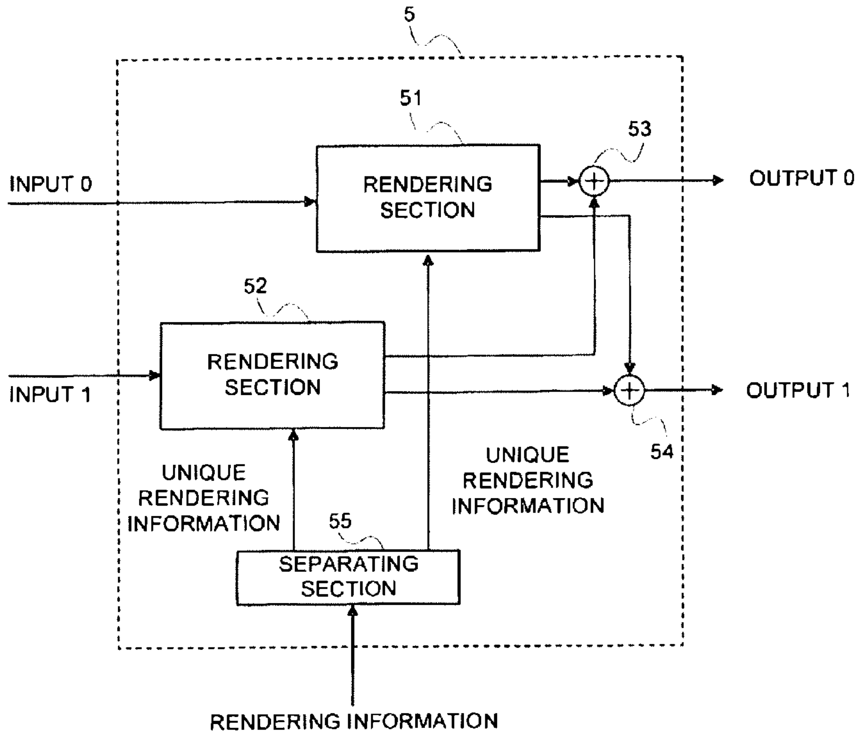
FIG. 2 An exemplary configuration of a multiple rendering section 5.
Figure 3:
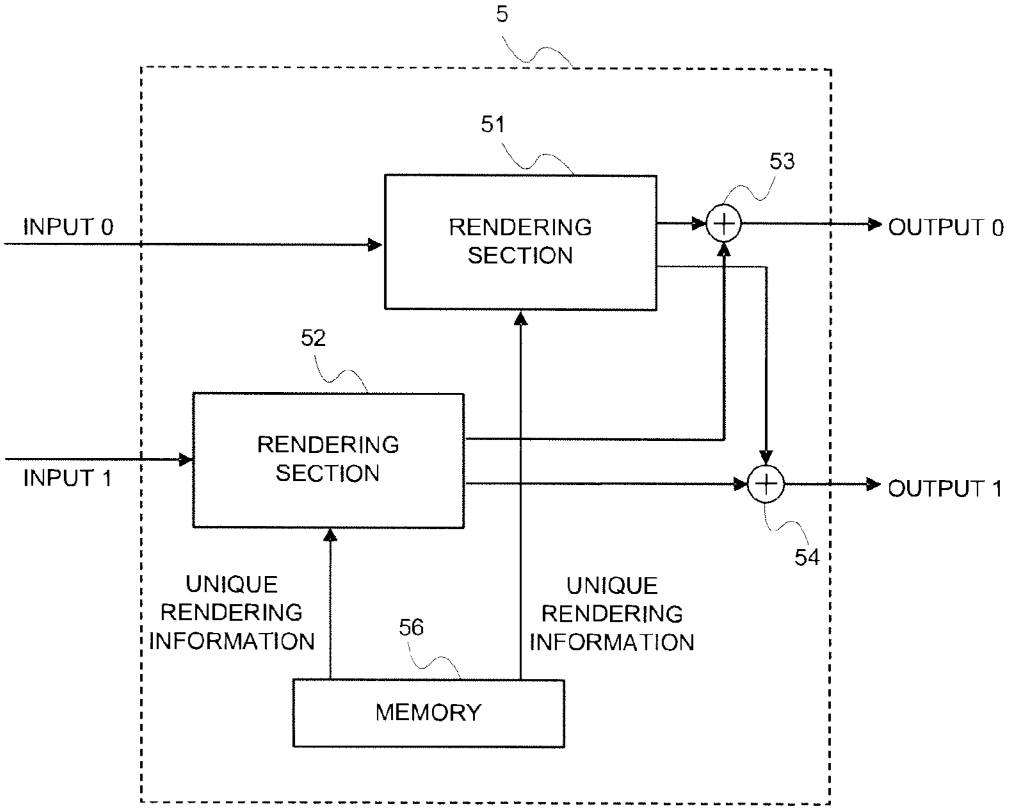
FIG. 3 A second exemplary configuration of the multiple rendering section 5.
Figure 4:
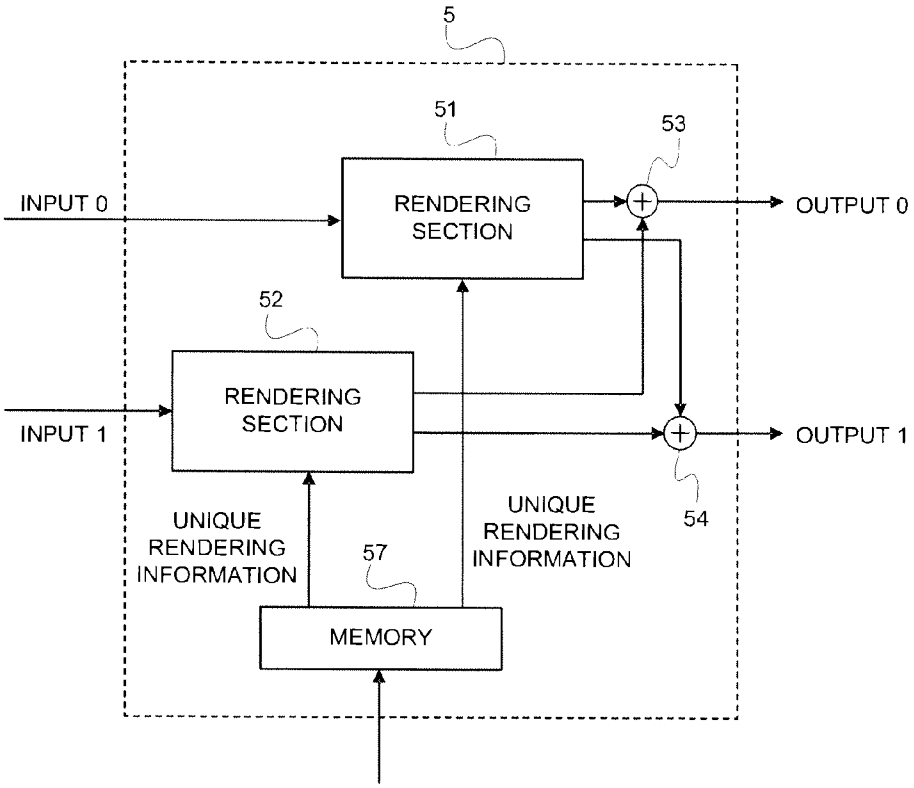
FIG. 4 A third exemplary configuration of the multiple rendering section 5.

The preceding description has addressed a case in which the number of input channels and the number of output channels in the multiple rendering section 5 are each two, i.e., $M_i=M_o=2$, with reference to FIGS. 2-4. However, the configurations shown in FIGS. 2-4 may be easily applied to the multiple rendering section 5 having a number of input channels and a number of output channels of one or three or more, without being limited to two. For example, it can be easily seen from the preceding description that the number of rendering sections included in the multiple rendering section 5 is equal to the number of inputs $M_i$, and the number of outputs of each rendering section (51, 52 or the like) is equal to the number of outputs $M_o$ of the multiple rendering section 5.

As described above, according to the first embodiment of the signal processing system of the present invention, rendering may be applied to a plurality of input signals containing varying proportions of signal components to impart different localization to them. Moreover, the signal processing system of the present embodiment can cause an input signal having an insufficient degree of signal separation to be perceived with lower distortion by using a separating function intrinsically given to the human auditory organ to further separate such a signal. That is, the signal processing system of the present embodiment can reduce distortion while maintaining performance of signal separation. There is thus provided a signal processing system capable of imparting localization to a plurality of signal components contained in an input signal with smaller distortion, the localization being differentiated from signal component to component.

Subsequently, a second embodiment of the signal processing system in the present invention will be described in detail referring to FIG. 5. The second embodiment of the present invention is for supplying pre-processed signals to the multiple rendering section 5.

Figure 5:
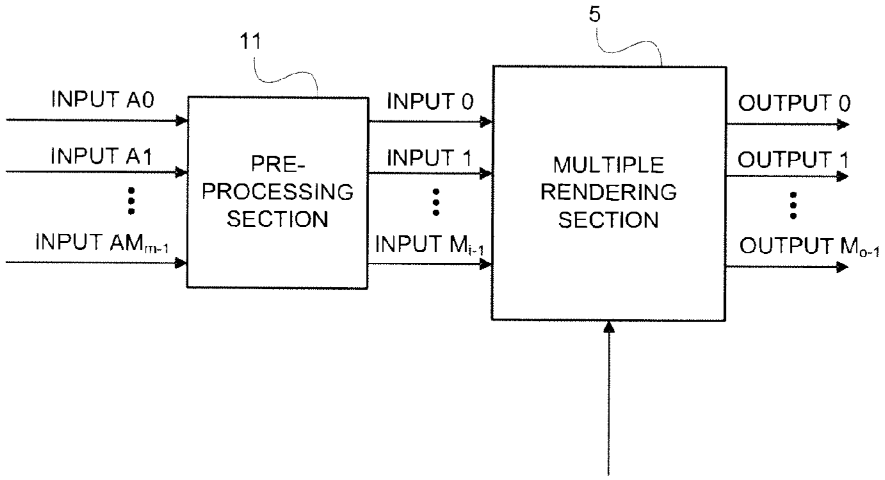
FIG. 5 A block diagram showing second embodiment of the present invention.

The signal processing system in FIG. 5 has a pre-processing section 11 disposed before the multiple rendering section 5. The pre-processing section 11 applies signal enhancement processing to an input signal. The pre-processing section 11 receives signals as input 0-input $M_{i-1}$ in which each signal component contained in the input signals is enhanced, and outputs them to the multiple rendering section 5. On receipt of input 0-input $M_{i-1}$, the multiple rendering section 5 imparts localization differentiated from input to input to them, and outputs the signals as output 0-output $M_{o-1}$. In FIG. 5, the configuration is made such that the rendering information is input to the multiple rendering section 5. However, a configuration in which the rendering information is kept in an internal memory, rather than inputting the rendering information from the outside, may be applied to the multiple rendering section 5, as discussed earlier with reference to FIG. 3. Moreover, a configuration in which a plurality of pieces of rendering information are stored in an internal memory and rendering selection information is input from the outside may be applied to the multiple rendering section 5, as discussed earlier with reference to FIG. 4. By using the pre-processing section 11, control to enhance a major signal component in an input signal may be achieved. Furthermore, it is also possible to increase the degree of separation between input signals, thus improving an effect of rendering following pre-processing.

Figure 6:
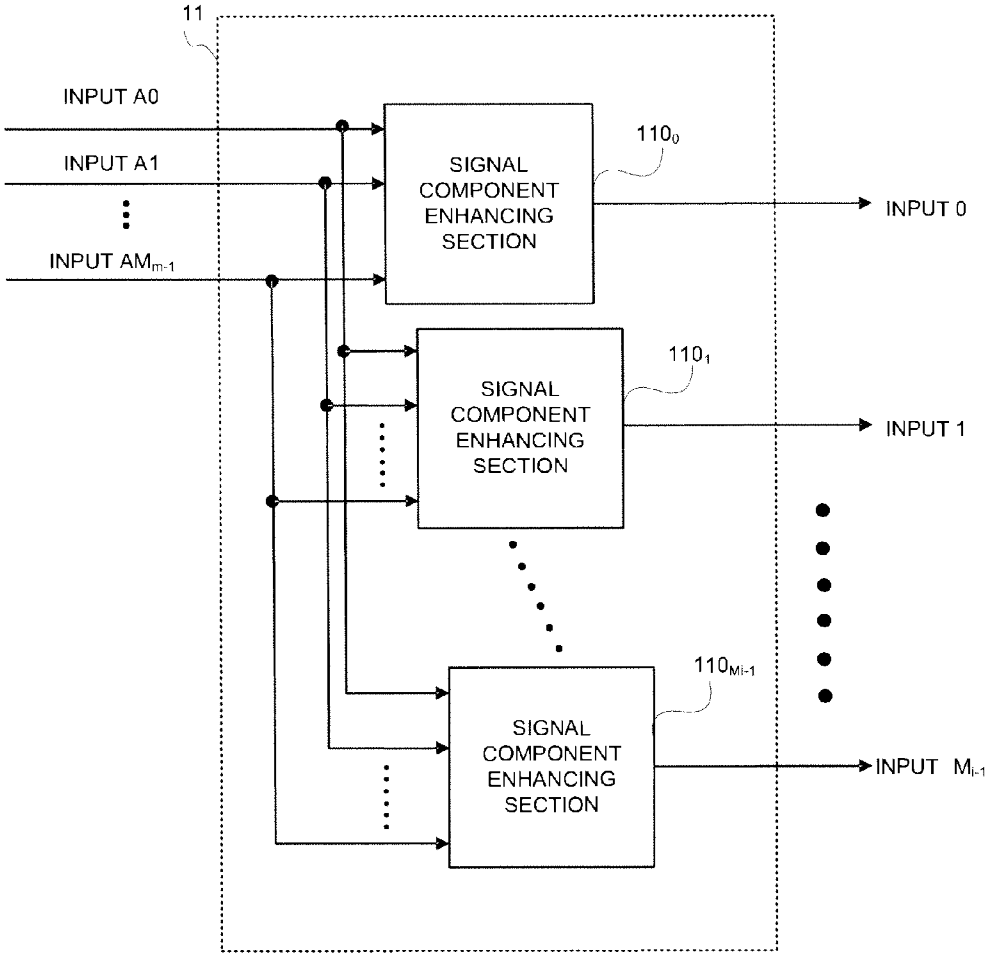
FIG. 6 An exemplary configuration of a pre-processing section 11.

Next, a first exemplary configuration of the pre-processing section 11 will be described in detail referring to FIG. 6. The pre-processing section 11 in FIG. 6 is comprised of a plurality of signal component enhancing sections 110$_0$-110$_{Mi-1}$. Outputs of the signal component enhancing sections 110$_0$-110$_{Mi-1}$ are output as input 0-input $M_{i-1}$, respectively. On receipt of input A0-input $AM_{i-1}$, the signal component enhancing section 110$_j$ ($0<j<M_{i-1}$) enhances a signal component j and outputs the resulting component as input j. The signal component enhancing sections 110$_0$-110$_{Mi-1}$ each may be constructed from a system using techniques referred to as directivity control, beamforming, blind source separation, independent component analysis, noise cancellation, and/or noise suppression.

For example, techniques related to directivity control and beamforming are disclosed in Non-patent Document 3 (Microphone Arrays, Springer, 2001) and Non-patent Document 4 (Speech Enhancement, Springer, 2005, pp. 229-246). Techniques related to methods of blind source separation and independent component analysis are disclosed in Non-patent Document 5 (Speech Enhancement, Springer, 2005, pp. 271-369). Moreover, techniques related to noise canceling are disclosed in Non-patent Document 6 (Proceedings of IEEE, Vol. 63, No. 12, 1975, pp. 1692-1715) and Non-patent Document 7 (IEICE Transactions of Fundamentals, Vol. E82-A, No. 8, 1999, pp. 1517-1525), and a technique related to a noise suppressor is disclosed in Patent Document 1.

Figure 7:
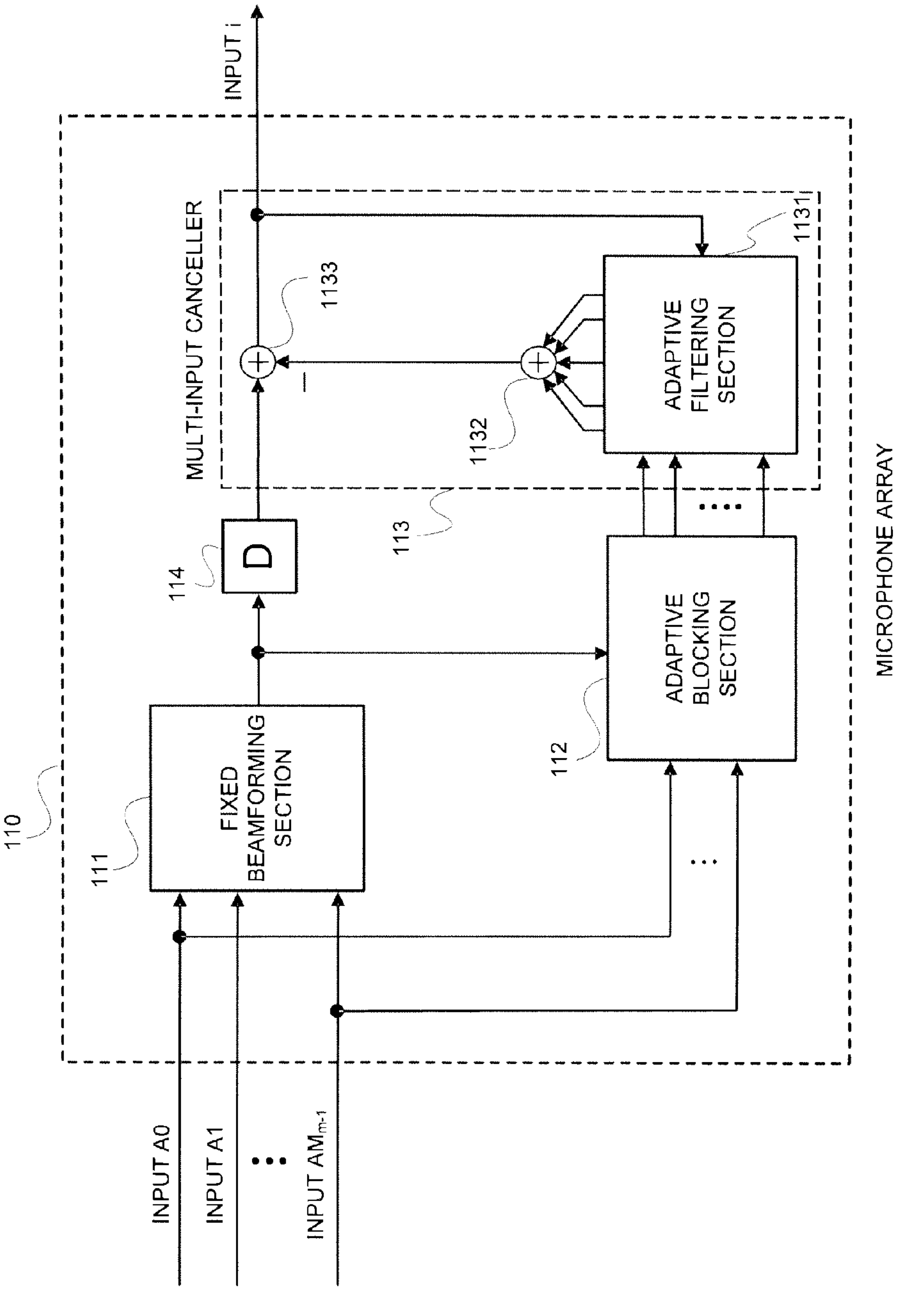
FIG. 7 An exemplary configuration of a signal component enhancing section 110.

Subsequently, an exemplary configuration of the signal component enhancing sections 110$_0$-110$_{Mi-1}$ will be described in detail referring to FIG. 7. One of the signal component enhancing sections 110$_0$-110$_{Mi-1}$ is illustrated in FIG. 7 as being constructed from a generalized sidelobe canceller (or Griffiths-Jim beamformer), which is a microphone array of one type. A signal component enhancing section 110$_j$ ($0<j<M_{i-1}$) is comprised of a fixed beamforming section 111, an adaptive blocking section 112, a delay element 114, and a multi-input canceller 113. The multi-input canceller is further comprised of an adaptive filtering section 1131, an adder 1132, and a subtractor 1133.

The input A0-input $AM_{i-1}$ are supplied to the fixed beamforming section 111 and adaptive blocking section 112. The fixed beamforming section 111 follows a predetermined desired signal coming direction, enhances a signal coming in the direction, and outputs the resulting signal to the adaptive blocking section 112 and delay element 114. Such a desired signal coming direction is defined as a coming direction for a signal component j in an input signal. The adaptive blocking section 112 employs an output of the fixed beamforming section 111 as a reference signal to operate so as to reduce or minimize a component correlated with the reference signal contained in input A0-input $AM_{i-1}$. Therefore, the desired signal is reduced or minimized at the output of the adaptive blocking section 112. The output of the adaptive blocking section 112 is output to the adaptive filtering section 1131. The delay element 114 delays an output signal of the fixed beamforming section 111 and outputs it to the subtractor 1133. The amount of delay at the delay element 114 is defined to compensate the delay in the adaptive filtering section 1131.

The adaptive filtering section 1131 is comprised of one or more adaptive filters. The adaptive filtering section 1131 employs an output of the adaptive blocking section 112 as a reference signal to operate so as to produce a signal component contained in the output of the delay element 114 and correlated with the reference signal. Signals produced at individual filters in the adaptive filtering section 1131 are output to the adder 1132. The outputs of the adaptive filtering section 1131 are added in the adder 1132, and the result is output to the subtractor 1133. The subtractor 1133 subtracts the output of the adder 1132 from the output of the delay element 114, and outputs the result as input j. That is, at the output of the subtractor 1133, a signal component not correlated with the output of the fixed beamforming section 111 is minimized relative to the output of the fixed beamforming section 111. The output of the subtractor 1133 is output as input j and also fed back to the adaptive filtering section 1131. The output of the subtractor 1133 is used in updating coefficients of the adaptive filter included in the adaptive filtering section 1131. The coefficients of the adaptive filtering section 1131 are updated so that the output of the subtractor 1133 is minimized. The adaptive filtering section 1131, adder 1132 and subtractor 1133 may be handled together as multi-input canceller 113. As described above, by configuring the pre-processing section 11 as a microphone array, spatial selectivity (directivity) can be controlled to enhance a specific signal.

A case in which the signal component enhancing sections $\mathbf{110}_0$-$\mathbf{110}_{Mi-1}$ are each constructed from a microphone array has been described referring to FIG. 7. Moreover, they may be constructed from a blind source separation system, an independent component analysis system, a noise canceling system, or a noise suppression system referring to Non-patent Documents 4-7. In any case, a similar effect to the configuration using a microphone array is provided.

Figure 8:
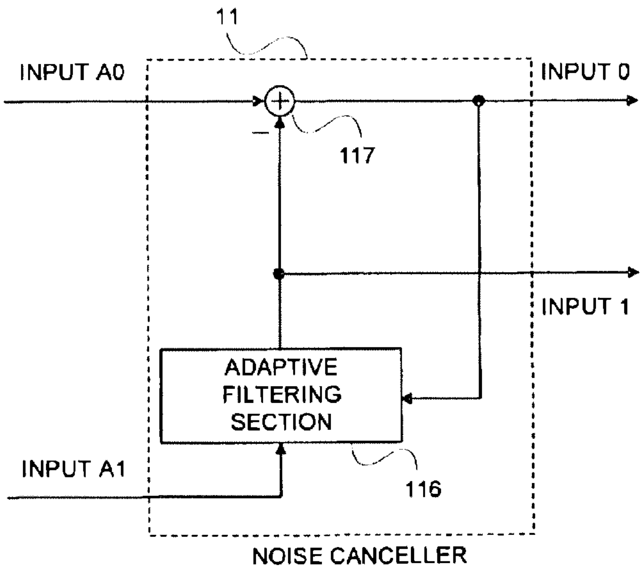
FIG. 8 A second exemplary configuration of the pre-processing section 11.

Next, a second exemplary configuration of the pre-processing section 11 will be described in detail referring to FIG. 8. The pre-processing section 11 in FIG. 8 is constructed from a noise canceller. Unlike the microphone array forming directivity, the noise canceller employs a signal correlated with a signal to be separated as a reference signal. Thus, the noise canceller can enhance or separate a specific signal more accurately than the microphone array that internally generates a reference signal. Moreover, in contrast to the microphone array that separates a signal based on directivity, the noise canceller separates a signal based on a difference in frequency spectrum between signals. Thus, it may be possible to increase the degree of separation by combining both. Furthermore, the microphone array can ordinarily provide a practical effect using signals from three or more microphones. However, the noise canceller can ordinarily provide a similar effect by two microphones. Thus, the pre-processing section 11 of the present exemplary configuration may be applied even in a case that the number of microphones is limited in view of cost or the like.

The pre-processing section 11 applies pre-processing to input A0 and input A1 and outputs input 0 and input 1. The noise canceller in the pre-processing section 11 is comprised of an adaptive filtering section 116 and a subtractor 117. Input A0 is supplied to the adaptive filtering section 116, and a filtered output is supplied to the subtractor 117. The adaptive filtering section 116 employs input A1 as a reference signal to operate so as to create a component correlated with the reference signal contained in input A0. The other input of the subtractor 117 is supplied with input A0. The subtractor 117 subtracts the output of the adaptive filtering section 116 from input A0, and outputs the result as input 0. The output of the subtractor 117 is fed back to the adaptive filtering section 116 at the same time, and used in updating coefficients of the adaptive filter included in the adaptive filtering section 116. The adaptive filtering section 116 updates the coefficients of the adaptive filter so that the output of the subtractor 117 received as an input is minimized. Thus, the output of the adaptive filtering section 116 is input A0 but with the signal component 0 removed, in which components other than the signal component 0 are dominant. The output of the adaptive filtering section 116 is output as input 1.

Figure 9:
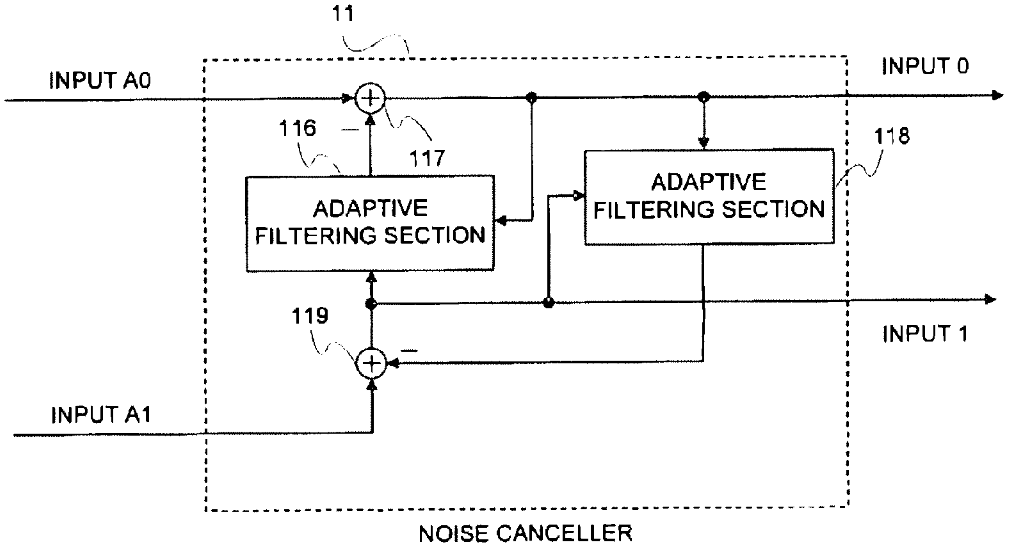
FIG. 9 A third exemplary configuration of the pre-processing section 11.

Next, a third exemplary configuration of the pre-processing section 11 will be described in detail referring to FIG. 9. The pre-processing section 11 in FIG. 9 is constructed from a noise canceller having a crosswise structure. The pre-processing section 11 applies pre-processing to input A0 and input A1, and outputs input 0 and input 1. The noise canceller in the pre-processing section 11 is comprised of adaptive filtering sections 116 and 118, and subtractors 117 and 119. Input A0 is supplied to the subtractor 119. The other input of the subtractor 119 is supplied with an output of the adaptive filtering section 118. The subtractor 119 subtracts the output of the adaptive filtering section 118 from input A1, and outputs the result to the adaptive filtering section 116. The adaptive filtering section 116 employs the output of the subtractor 119 as a reference signal to operate so as to create a component contained in input A0 correlated with the reference signal. The output of the adaptive filtering section 116 is supplied to the subtractor 117. The other input of the subtractor 117 is supplied with input A0. The subtractor 117 subtracts the output of the adaptive filtering section 116 from input A0, and outputs the result as input 0.

The output of the subtractor 117 is fed back to the adaptive filtering section 116 as an error at the same time, and is used in updating coefficients of the adaptive filter included in the adaptive filtering section 116. The adaptive filtering section 116 updates the coefficients of the adaptive filter so that the output of the subtractor 117 supplied as an error is minimized. The output of the subtractor 117 is also output to the adaptive filtering section 118. The adaptive filtering section 118 employs the output of the subtractor 117 as a reference signal to operate so as to create a component contained in input A1 correlated with the reference signal. Therefore, at the output of the subtractor 119, a dominant signal component of input 0 is eliminated, and a dominant element in input A1 becomes a main signal component. The output of the subtractor 119 is supplied as input A1. Moreover, the output of the subtractor 119 is fed back to the adaptive filtering section 118, and is used in updating coefficients of the adaptive filter included in the adaptive filtering section 118. The adaptive filtering section 118 updates the coefficients of the adaptive filter so that the output of the subtractor 119 supplied as an error is minimized.

The second exemplary configuration is made such that a dominant signal component of input A0 is leaked into input 1. However, the third exemplary configuration can produce input 1 without any leakage of the dominant signal component of input A0. This is because the adaptive filtering section 118 and subtractor 119 are used to eliminate leakage of the dominant signal component of input A0. Thus, performance of signal separation in a signal output as input 1 (the output of the subtractor 119) is improved.

Figure 10:
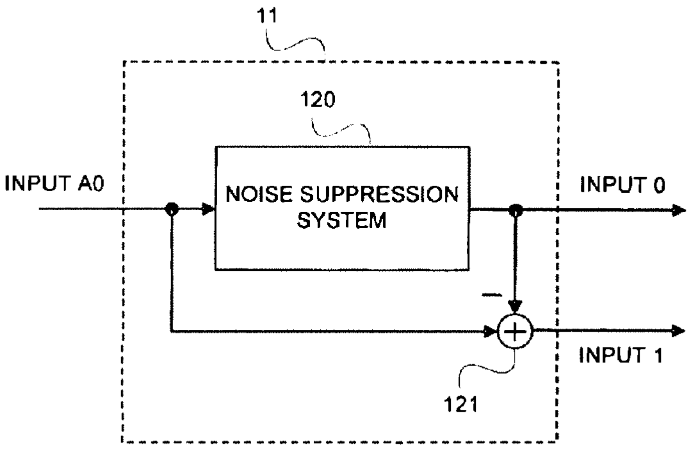
FIG. 10 A fourth exemplary configuration of the pre-processing section 11.

Next, a fourth exemplary configuration of the pre-processing section 11 will be described in detail referring to FIG. 10. In the fourth exemplary configuration shown in FIG. 10, the pre-processing section 11 is constructed from a single-input noise suppression system (noise suppressor) 120 and a subtractor 121. Unlike the first-third configurations of the pre-processing section 11, the input of the pre-processing section 11 is for a single signal, and the output is for two signals represented as input 0 and input 1. On receipt of input A0, the noise suppression system 120 enhances a dominant signal component therein and outputs the result as input 0. The output of the noise suppression system 120 is also output to the subtractor 121 at the same time. The other input of the subtractor 121 is supplied with input A0. The subtractor 121 subtracts the output of the noise suppression system, i.e., a dominant signal component of input A0, from input A0, and outputs the result as input 1. Therefore, in input 1, components other than the main signal component in input A0 become dominant. Thus, separation of a signal in input A0 with single signal is achieved.

Figure 11:
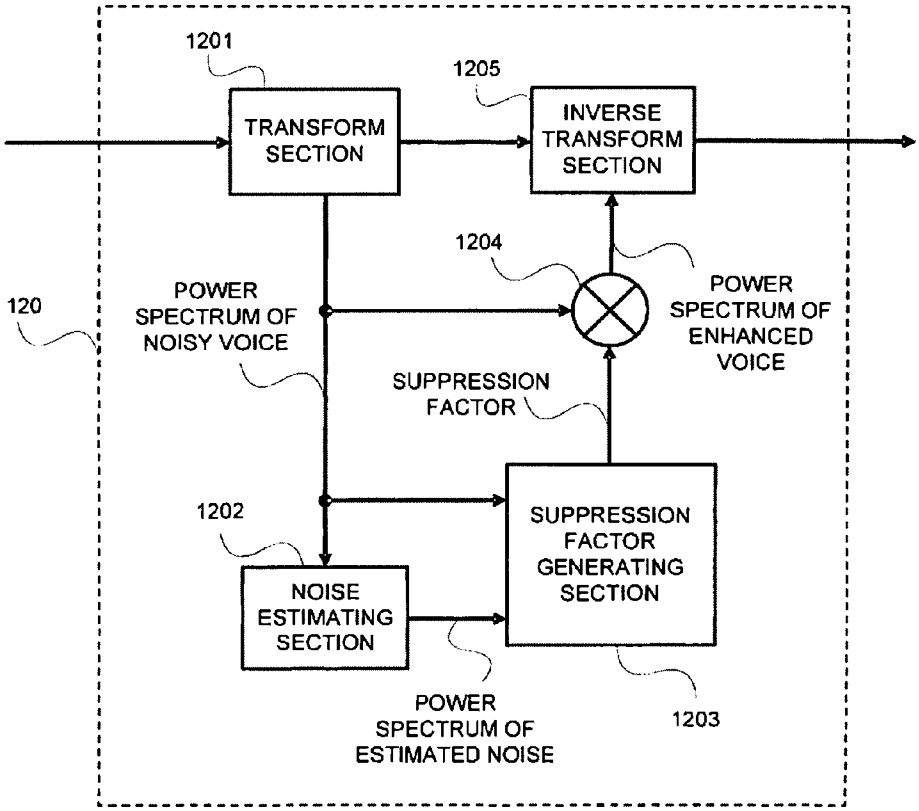
FIG. 11 An exemplary configuration of a noise suppression system 120.

Subsequently, an exemplary configuration of a noise suppression system 120 will be described in detail referring to FIG. 11. The noise suppression system 120 is comprised of a transform section 1201, a noise estimating section 1202, a suppression factor generating section 1203, a multiplier 1204, and an inverse transform section 1205. The transform section 1201 is supplied with input A0, and the output of the inverse transform section 1205 is output as input 0. The transform section 1201 gathers a plurality of input signal samples contained in input A0 to compose one block, and applies frequency transform to each block. Frequency transform that may be employed includes Fourier transform, cosine transform, and KL (Karhunen-Loève) transform. Techniques and properties related to specific calculation for these transform are disclosed in Non-patent Document 8 (Digital Coding of Waveforms, Principles and Applications to Speech and Video, Prentice-Hall, 1990).

Moreover, the transform section 1201 may apply the transform described above to input signal samples for one block weighted by a window function. Such window functions that are known may include hamming, hanning (hann), Kaiser, and Blackman window functions. A more complex window function may be employed. Techniques related to these window functions are disclosed in Non-patent Document 9 (Digital Signal Processing, Prentice-Hall, 1975) and Non-patent Document 10 (Multirate Systems and Filter Banks, Prentice-Hall, 1993).

The transform section 1201 may allow overlap between blocks when constructing one block from a plurality of input signal samples contained in input A0. For example, when overlap with a block length of 30% is employed, the last 30% of signal samples in a certain block are employed as the first 30% of signal samples in a next block, so that the samples are duplicatively employed over a plurality of blocks. A technique related to block clustering and transform with overlap is disclosed in Non-patent Document 8.

Moreover, the transform section 1201 may be constructed from a frequency division filter bank. The frequency division filter bank is comprised of a plurality of band-pass filters. The frequency division filter bank divides a received input signal into a plurality of frequency bands and outputs the resulting signal. The frequency bands in the frequency division filter bank may be at regular or irregular intervals. Frequency division at irregular intervals allows the frequency to be divided into narrower bands in a lower band in which many important components of voice are contained, thereby reducing temporal resolution, while it allows the frequency to be divided into broader bands in a higher band, thereby improving temporal resolution. Division at irregular intervals may employ octave division where the band is sequentially halved toward a lower range or critical frequency division corresponding to human auditory properties. A technique related to a frequency division filter bank and a method of designing the same is disclosed in Non-patent Document 10.

The transform section 1201 outputs a power spectrum of noisy voice to the noise estimating section 1202, suppression factor generating section 1203, and multiplier 1204. The power spectrum of noisy voice is information on the amplitude of frequency-transformed signal components. The transform section 1201 outputs information on the phase of the frequency-transformed signal components to the inverse transform section 1205. The noise estimating section 1202 estimates a plurality kinds of noise based on information on a plurality of frequencies/amplitudes contained in the input power spectrum of noisy voice, and outputs the result to the suppression factor generating section 1203. The suppression factor generating section 1203 uses the input information on the plurality of the frequencies/amplitudes and the estimated plurality of kinds of noise to generate a plurality of suppression factors respectively corresponding to these frequencies. The suppression factors are generated so that the factor increases for a larger ratio of the frequency-amplitude and estimated noise, and takes a value between zero and one. In determining the suppression factors, a method disclosed in Patent Document 1 may be employed. The suppression factor generating section 1203 outputs the plurality of suppression factors to the multiplier 1204. The multiplier 1204 applies weight to the power spectrum of noisy voice supplied from the transform section 1201 with the plurality of suppression factors supplied from the suppression factor generating section 1203, and outputs the resulting power spectrum of enhanced voice to the inverse transform section 1205.

The inverse transform section 1205 applies inverse transform to information reconstructed from the power spectrum of enhanced voice supplied from the multiplier 1204 and the phase supplied from the transform section 1201, and outputs the result as input 0. The inverse transform applied by the inverse transform section 1205 is desirably selected as inverse transform corresponding to the transform applied by the transform section 1201. For example, when the transform section 1201 gathers a plurality of input signal samples together to construct one block and applies frequency transform to the block, the inverse transform section 1205 applies corresponding inverse transform to the same number of samples. Moreover, in a case that overlap is allowed between blocks when the transform section 1201 constructs one block from a plurality of input signal samples, the inverse transform section 1205 correspondingly applies the same overlap to the inverse-transformed signals. Furthermore, when the transform section 1201 is constructed from a frequency division filter bank, the inverse transform section 1205 is constructed from a band-synthesis filter bank. A technique related to the band-synthesis filter bank and a method of designing the same is disclosed in Non-patent Document 10.

The fourth exemplary configuration of the pre-processing section 11 is capable of separating a signal component from one input (input A0, in this case), unlike the first-fourth exemplary configurations in which a plurality of input signals are input to the pre-processing section 11. This is because a dominant signal component in input A0 is enhanced and subtracted from input A0 to generate non-dominant signal components.

Figure 12:
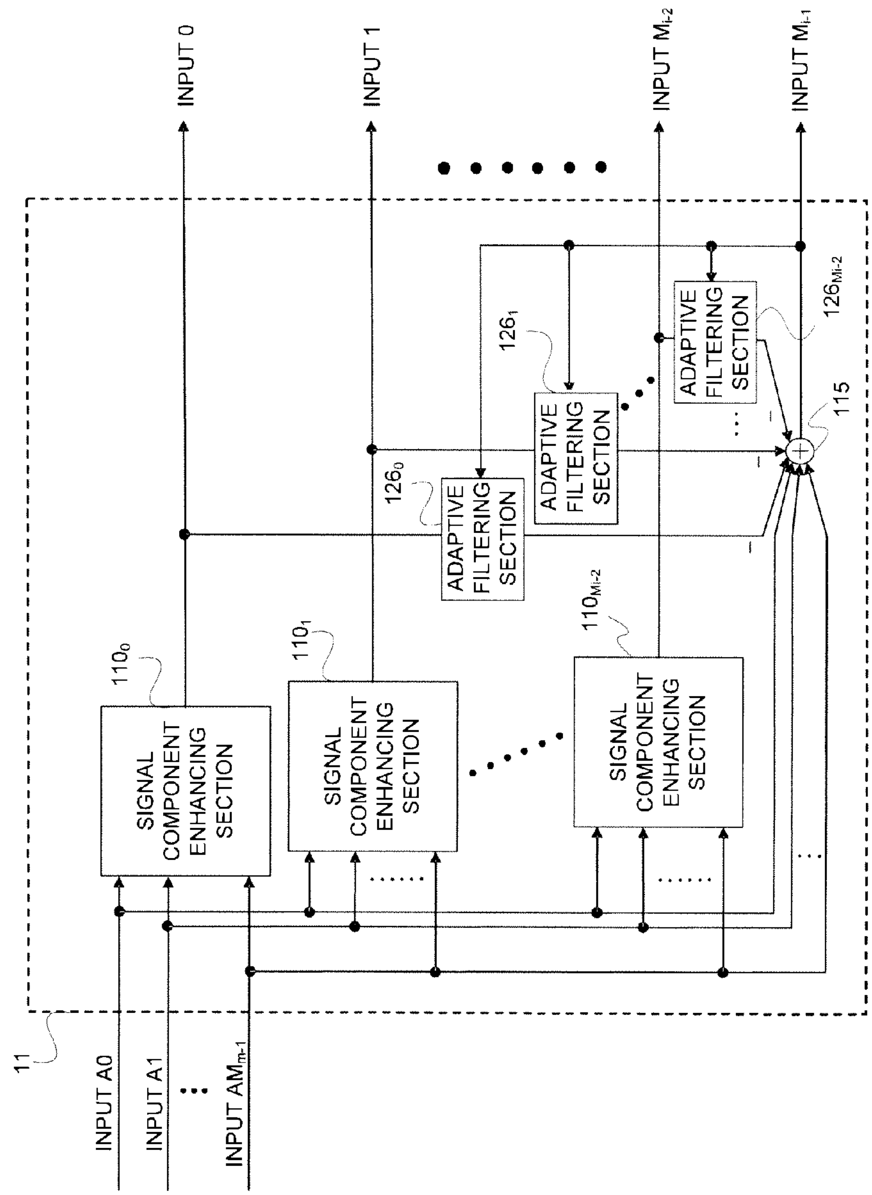
FIG. 12 A fifth exemplary configuration of the pre-processing section 11.

Next, referring to FIG. 12, a fifth exemplary configuration of the pre-processing section 11 will be described in detail. The pre-processing section 11 in FIG. 12 is comprised of signal component enhancing sections $\mathbf{110}_0$-$\mathbf{110}_{Mi-2}$, adaptive filtering sections $\mathbf{126}_0$-$\mathbf{126}_{Mi-2}$, and an adder 115. The outputs of the signal component enhancing sections $\mathbf{110}_0$-$\mathbf{110}_{Mi-2}$ are output as input 0-input $M_{i-2}$, and the output of the adder 115 is output as input $M_{i-1}$. The signal component enhancing section $\mathbf{110}_j$ ($0 \le j \le M_{i-2}$) operates as described regarding the first exemplary configuration in FIG. 6. The adaptive filtering sections $\mathbf{126}_0$-$\mathbf{126}_{Mi-2}$ are supplied with outputs of the signal component enhancing sections $\mathbf{110}_0$-$\mathbf{110}_{Mi-2}$, respectively, to generate signal components correlated with the inputs. The outputs of the adaptive filtering sections $\mathbf{126}_0$-$\mathbf{126}_{Mi-2}$ are supplied to the adder 115 after inverting all their polarities. The other input of the adder 115 is supplied with input A0-input $AM_{i-1}$. The adder 115 subtracts a total sum of the outputs of the adaptive filtering sections $\mathbf{126}_0$-$\mathbf{126}_{Mi-2}$ from the total sum of input A0-input $AM_{i-1}$, and outputs a result thereof as input $M_{i-1}$. Therefore, the output of the adder 115 does theoretically not contain the signal components enhanced at the signal component enhancing sections $\mathbf{110}_0$-$\mathbf{110}_{Mi-2}$. The output of the adder 115 is fed back to the adaptive filtering sections $\mathbf{126}_0$-$\mathbf{126}_{Mi-2}$. The adaptive filtering sections $\mathbf{126}_0$-$\mathbf{126}_{Mi-2}$ update the coefficients of the adaptive filters contained in the adaptive filtering sections $\mathbf{126}_0$-$\mathbf{126}_{Mi-2}$ so that the output of the adder 115 is minimized.

Moreover, the pre-processing section 11 of the present exemplary configuration may have a configuration in which the outputs of the signal component enhancing sections $\mathbf{110}_0$-$\mathbf{110}_{Mi-2}$ are directly output to the adder 115 without using the adaptive filtering sections $126_0$-$126_{Mi-2}$, or a configuration in which the adder 115 simply adds input 0-input $M_{i-2}$. In these cases, a similar effect to that by the pre-processing section 11 in the present exemplary configuration can be provided.

The pre-processing section 11 in the fifth exemplary configuration comprises the adaptive filtering sections $126_0$-$126_{Mi-2}$ and adder 115, unlike the pre-processing section 11 in the first exemplary configuration described with reference to FIG. 6. By such a configuration, the pre-processing section 11 in the fifth exemplary configuration outputs a signal as input $M_{i-1}$ not containing signals enhanced at the outputs of the signal component enhancing sections $110_0$-$110_{Mi-2}$. In input $M_{i-1}$, diffusive signals, such as background noise that is generally uniformly present in space, are dominant. Thus, it is possible to enhance diffusive signals by providing the adaptive filtering sections $126_0$-$126_{Mi-2}$ and adder 115 in the pre-processing section 11.

Figure 13:
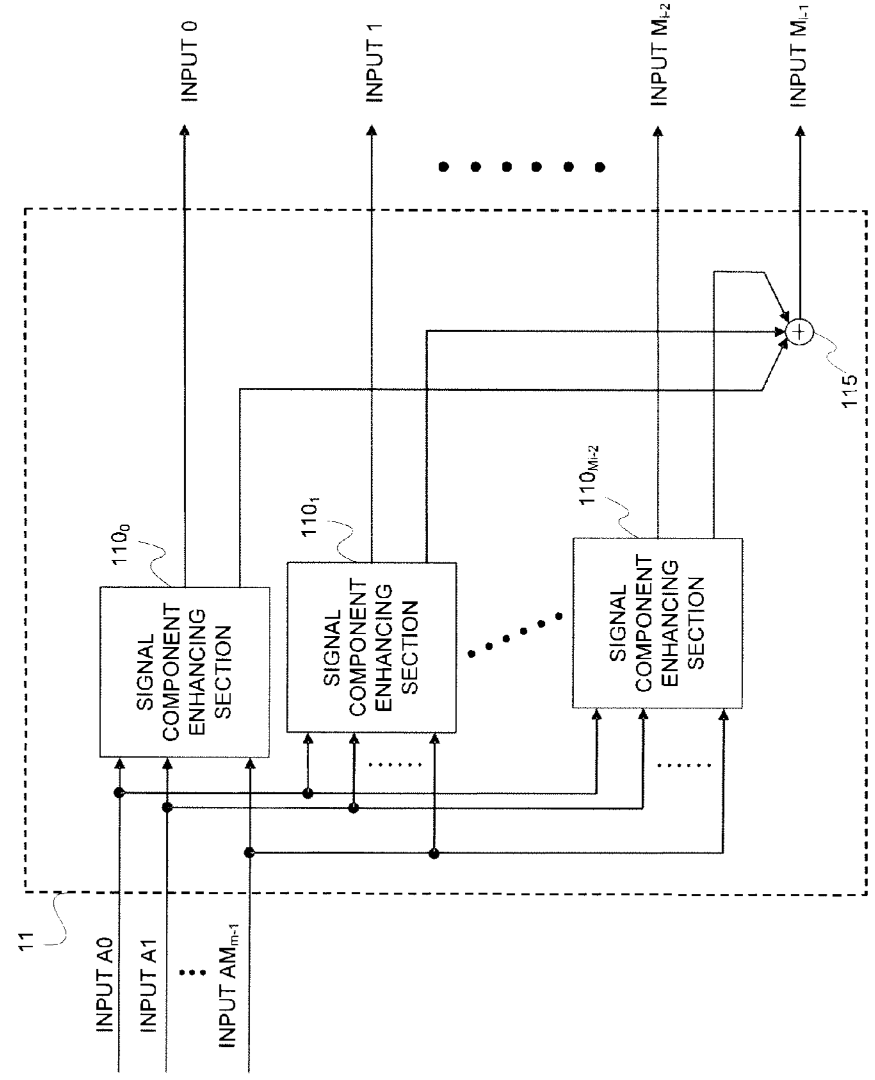
FIG. 13 A sixth exemplary configuration of the pre-processing section 11.

Next, a sixth exemplary configuration of the pre-processing section 11 will be described in detail referring to FIG. 13. The pre-processing section 11 shown in FIG. 13 is comprised of a plurality of signal component enhancing sections $110_0$-$110_{Mi-2}$ and an adder 115. The outputs of the signal component enhancing section $110_0$-$110_{Mi-2}$ are output as input 0-input $M_{i-2}$, and the output of the adder 115 is output as input $M_{i-1}$. In a case that the signal component enhancing section $110_j$ ($0 \le j \le M_{i-2}$) is constructed from a generalized sidelobe canceller, a signal internally subtracted from the output of the fixed beamforming section has signal components (non-enhanced components) other than enhanced ones. Therefore, a signal having non-enhanced components is extracted from each of the signal component enhancing sections $110_0$-$110_{Mi-2}$, and added at the adder 115. Thus, no enhanced signal component is contained in the output of the adder 115.

Figure 14:
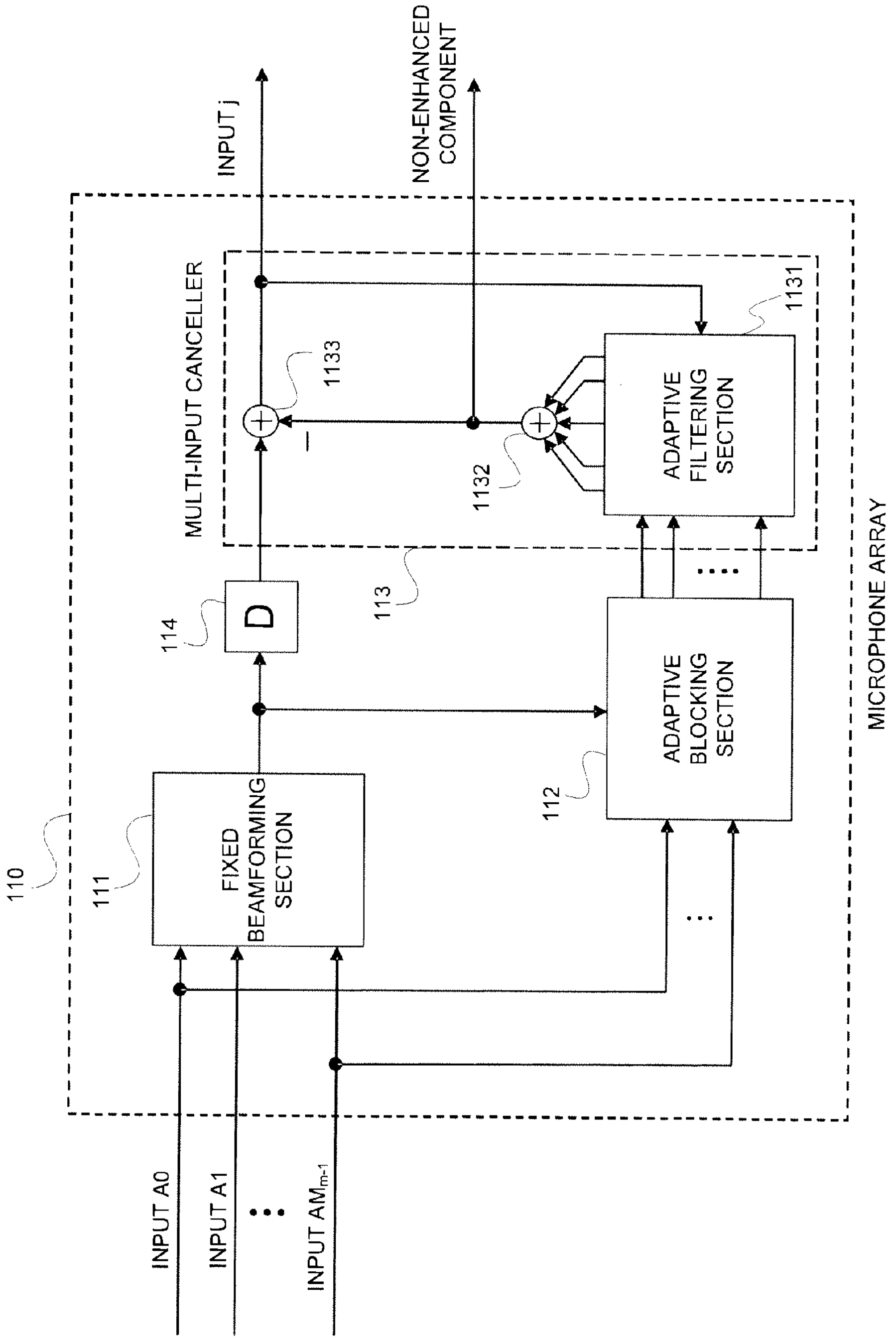
FIG. 14 A second exemplary configuration of the signal component enhancing section 110.

An example of the generalized sidelobe canceller is shown in FIG. 14. The generalized sidelobe canceller shown in FIG. 14 has a similar configuration to that shown in FIG. 7. According to the generalized sidelobe canceller shown in FIG. 14, the output of the adder 1132 is output as a non-enhanced component, unlike the generalized sidelobe canceller shown in FIG. 7. By adding such non-enhanced components at the adder 115 shown in FIG. 13, they can be enhanced as a diffusive signal. Likewise, any configuration that allows for acquisition of non-enhanced components may be employed as the signal component enhancing section, besides the generalized sidelobe canceller.

The pre-processing section 11 in the sixth exemplary configuration newly has the adder 115, and outputs non-enhanced components each obtained from the signal component enhancing sections $110_0$-$110_{Mi-2}$ as input $M_{i-1}$, unlike the first exemplary configuration described earlier with reference to FIG. 6. By such a configuration, diffusive signals, such as background noise that is generally uniformly present in space, are dominant in input $M_{i-1}$. Thus, it is possible to enhance the non-enhanced component as diffusive signals by providing the adaptive filtering sections $126_0$-$126_{Mi-2}$ and adder 115 in the pre-processing section 11.

As described above, according to the second embodiment of the signal processing system in the present invention, rendering may be applied to a plurality of input signals containing varying proportions of signal components to impart different localization to them. Moreover, the signal processing system of the present embodiment applies pre-processing to a plurality of input signals to enhance a specific signal component contained in the signals and improve the degree of separation, before applying rendering. Furthermore, the signal processing system of the present embodiment can cause an input signal having an insufficient degree of signal separation to be further separated and perceived with lower distortion by using a separating function intrinsically given to the human auditory organ. That is, the signal processing system of the present embodiment can reduce distortion while maintaining performance of signal separation. There is thus provided a signal processing system capable of imparting localization to a plurality of signal components contained in an input signal with smaller distortion, the localization being differentiated from signal component to component.

Figure 15:
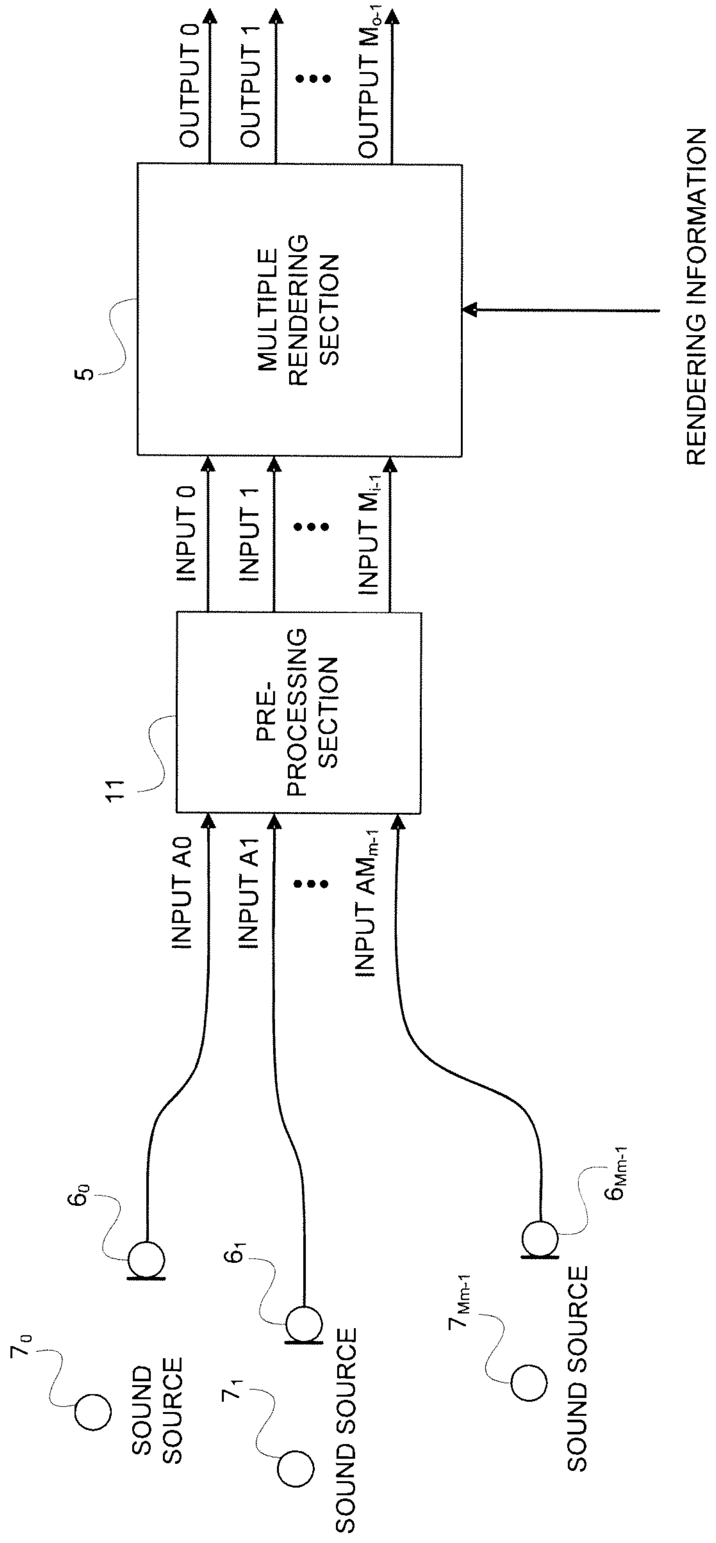
FIG. 15 A block diagram showing a third embodiment of the present invention.

Subsequently, a third embodiment of the signal processing system in the present invention will be described in detail referring to FIG. 15. The third embodiment of the present invention is for capturing signals input to the multiple rendering section 5 by a microphone. Now a system for inputting an input signal to the multiple rendering section 5 via a microphone will be described referring to FIG. 15.

The pre-processing section 11 is supplied with input A0-$AM_{m-1}$ from microphones $6_0$-$6_{Mm-1}$. The microphone $6_0$ is disposed near a sound source $7_0$ that generates a signal component 0, the microphone $6_1$ is disposed near a sound source $7_1$ that generates a signal component 1, and similarly, the microphone $6_{Mm-1}$ is disposed near a sound source $7_{Mm-1}$ that generates a signal component $M_{m-1}$. Thus, the signal component 0 is enhanced in input A0, the signal component 1 is enhanced in input A1, and the signal component $M_{m-1}$ is enhanced in input $AM_{m-1}$. By supplying the resulting input A0-$AM_{m-1}$ into the pre-processing section 11, the signal components 0-$M_{m-1}$ can be localized at different positions in space. It should be noted that directive microphones may be employed for the microphones $6_0$-$6_{Mm-1}$ and their directivity may be made to coincide with the sound source to thereby further improve the effect described above. Moreover, a similar effect may be obtained even in a configuration without the pre-processing section 11.

As described above, according to the third embodiment of the signal processing system of the present invention, rendering may be applied to a plurality of input signals containing varying proportions of signal components to impart different localization to them. Moreover, since a plurality of input signals are captured using microphones disposed near sound sources for a desired signal component, rendering can be achieved after improving the degree of separation between microphone signals. There is thus provided a signal processing system capable of imparting localization to a plurality of signal components contained in an input signal with smaller distortion, the localization being differentiated from signal component to component.

Figure 16:
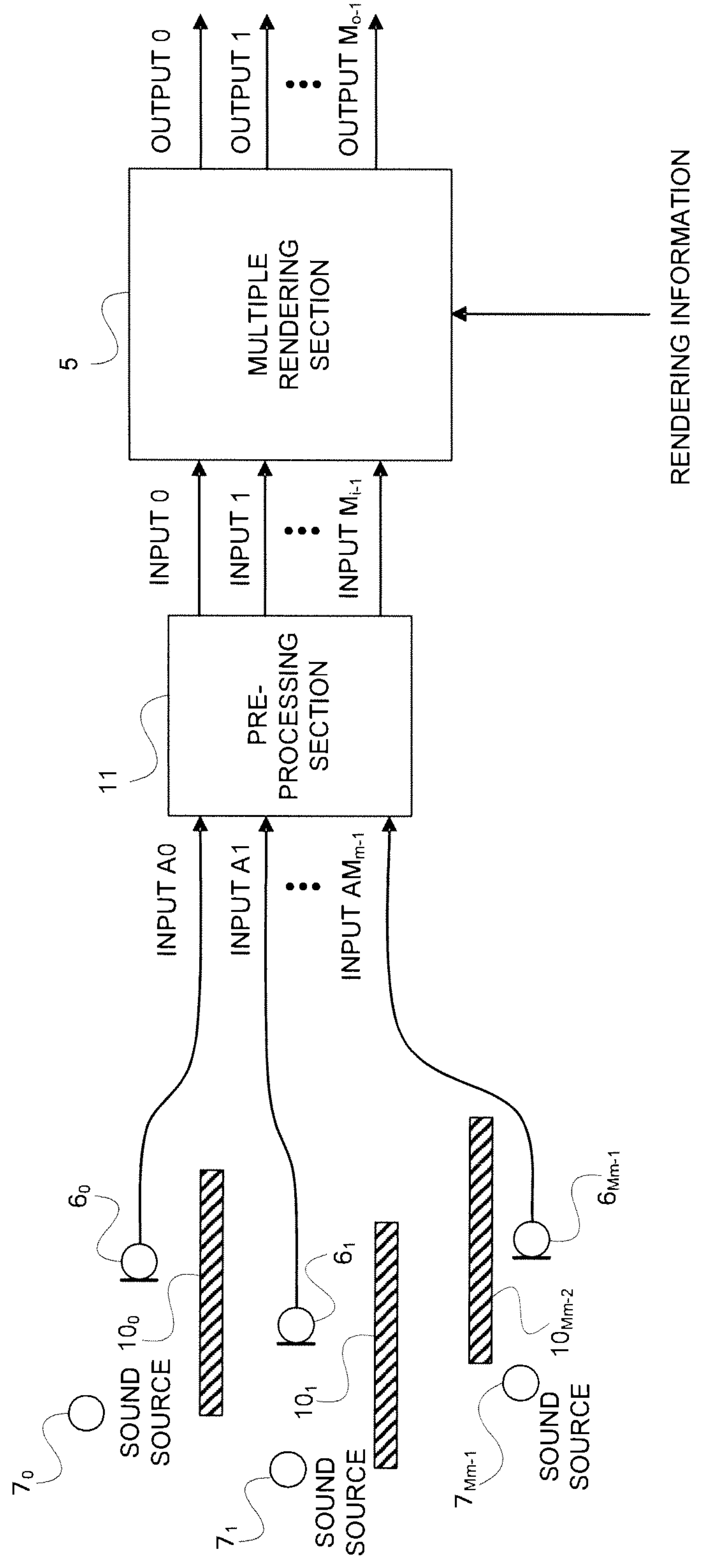
FIG. 16 A block diagram showing a fourth embodiment of the present invention.

Subsequently, a fourth embodiment of the signal processing system in the present invention will be described in detail referring to FIG. 16. The fourth embodiment of the present invention comprises an obstacle between microphones for capturing signals input to the pre-processing section 11 to reduce leakage of the signals. In FIG. 16, there are wall-like obstacles $10_0$-$10_{Mm-1}$ between each pair of microphones $6_0$-$6_{Mm-1}$. As shown in FIG. 15, signals may leak from the sound source $7_1$ to the microphone $6_0$, or from the sound source $7_0$ to the microphone $6_1$ in practice when the microphones are disposed in a free space. In the signal processing system in the present embodiment, the obstacles $10_0$-$10_{Mm-1}$ may be appropriately disposed to reduce such signal leakage. The obstacles $10_0$-$10_{Mm-1}$ are disposed to provide an effect of deliberately attenuating signals. For example, when the obstacle $10_0$ lies to intercept a straight line connecting the sound source $7_0$ and microphone $6_1$, a signal component 0 in signals generated by the sound source 7 is attenuated to reach the microphone $6_1$. The amount of attenuation when the signal component 0 reaches the microphone $6_0$ with no obstacle $10_0$ lying on the propagation path is smaller than that of the signal reaching the microphone $6_1$. In other words, the power of the signal component 0 is greater when it is contained in the input signal from the microphone $6_0$ than that contained in the input signal from the microphone $6_1$. According to a similar discussion, the power of the signal component 1 is greater when it is contained in the input signal from the microphone $6_1$ than that contained in the input signal from the microphone $6_0$. Thus, the signal component 0 generated by the sound source $7_0$ is dominant in input A0, while the signal component 1 generated by the sound source $7_1$ is dominant in input A1.

Figure 17:
FIG. 17 An example in which two microphones are provided on front and rear surfaces of a cell phone.

Objects other than the obstacles as described above may be employed to provide the effect of attenuating signals. For example, a plurality of microphones, which are provided to different side surfaces of a terminal such as a cell phone, may be employed. Especially, a microphone provided one surface of a housing and that provided on another surface cause the housing itself to serve as an obstacle, so that a similar effect to that by the signal processing system described above may be provided. FIG. 17 shows such an example. In the example shown in FIG. 17, the cell phone is provided on its one surface with the microphone $6_0$ and on the other surface with the microphone $6_1$.

Figure 18:
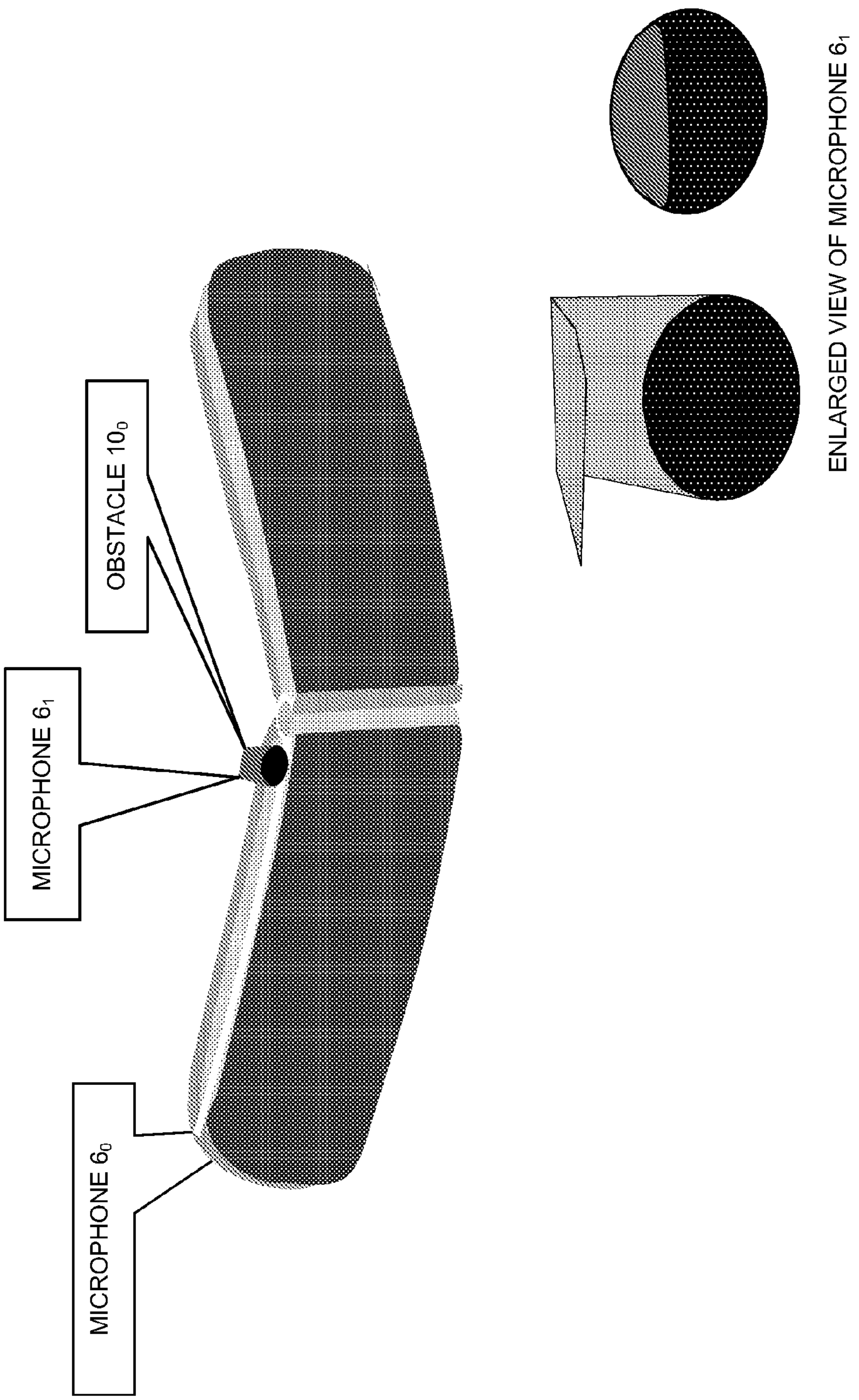
FIG. 18 An example in which two microphones are provided on front and side surfaces of a cell phone.

FIG. 18 shows an example of microphones provided on a front surface and a side surface of a cell phone. The microphone $6_1$ is fixed to a side surface, in contrast to the microphone $6_0$. Moreover, the microphones $6_0$ and $6_1$ may be provided with a panel-like protrusion for reducing signal leakage from the other microphone. This is illustrated in an enlarged view taking the microphone $6_1$ as an example.

Figure 19:
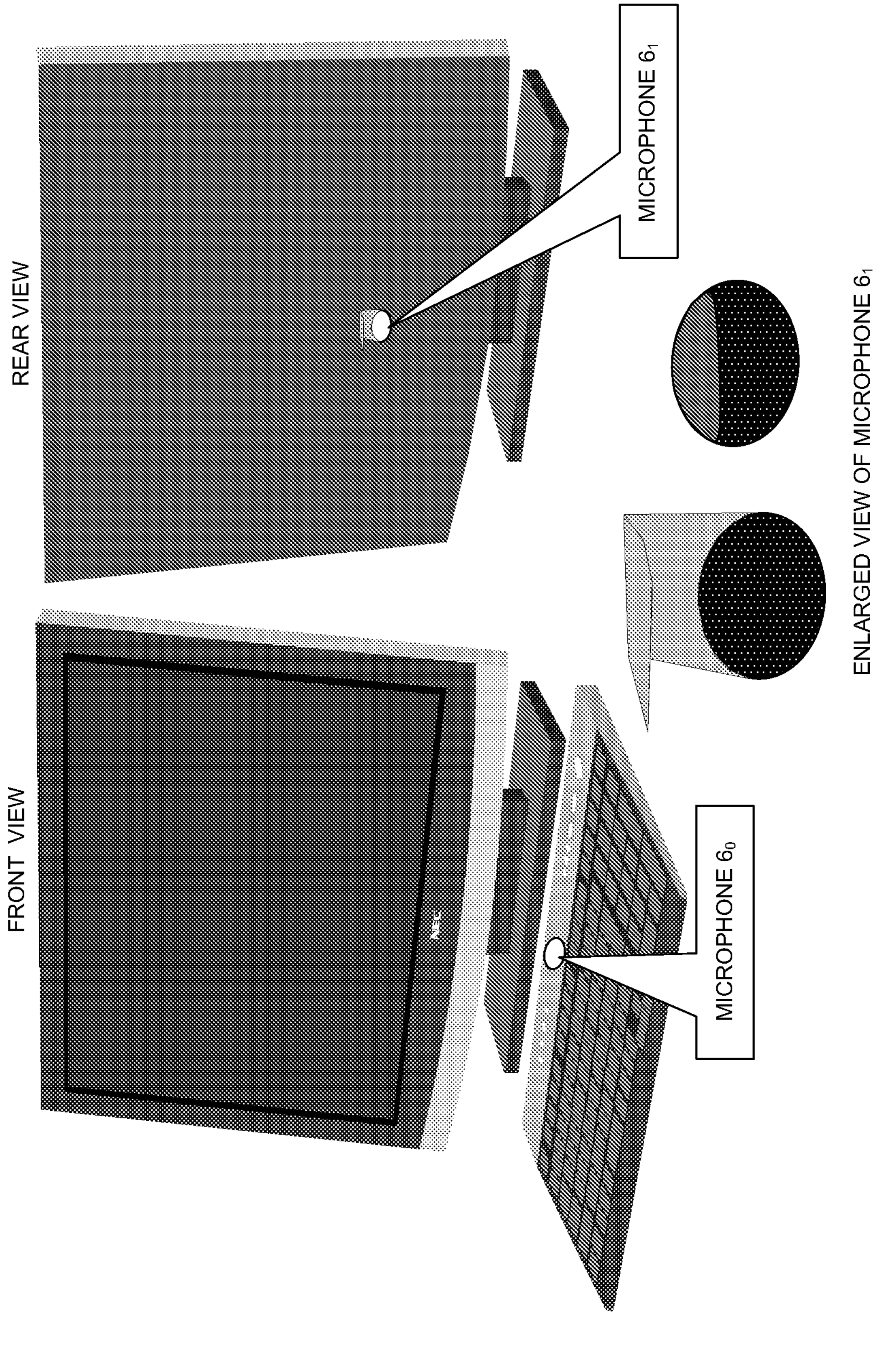
FIG. 19 An example in which two microphones are provided at an upper surface of a keyboard and a rear surface of a display device in a PC.
Figure 20:
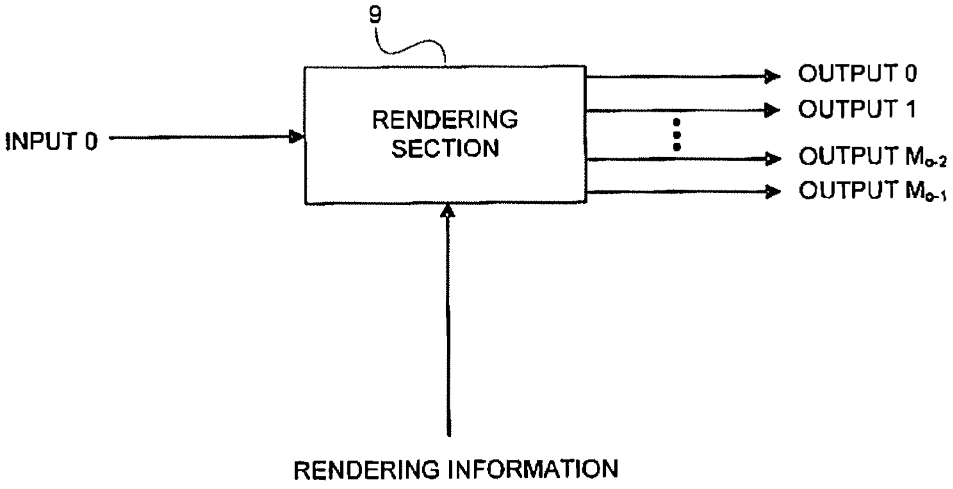
FIG. 20 A block diagram showing a related technique.

A similar effect to that in the configuration of the terminal such as a cell phone described above may be obtained by microphones provided on a keyboard and on a display device of a personal computer (PC). Especially in a case that a microphone is provided on a rear side of the display device, a similar effect to that in the configuration of the terminal such as the cell phone described above may be obtained because the display device itself serves as an obstacle. FIG. 19 shows such an example. A keyboard in the front view is attached with a microphone $6_0$, and a rear surface of the display device in the rear view is attached with a microphone $6_1$. Moreover, the microphones $6_0$ and $6_1$ may be provided with a panel-like protrusion for reducing signal leakage from the other microphone. This is illustrated in an enlarged view taking the microphone $6_1$ as an example. Microphones attached to the side surface of the PC and that of the display device may provide a similar effect to that in the configuration of the terminal such as the cell phone described above.

As described above, according to the fourth embodiment of the signal processing system of the present invention, rendering may be applied to a plurality of input signals containing varying proportions of signal components to impart different localization to them. Moreover, since a plurality of input signals are captured using microphones disposed near sound sources for a desired signal component, rendering can be achieved after improving the degree of separation between microphone signals. Furthermore, by disposing an obstacle for reducing mutual signal leakage between microphones, rendering can be achieved after further improving the degree of separation between the microphone signals. Moreover, the signal processing system of the present embodiment can cause an input signal having an insufficient degree of signal separation to be further separated and perceived with lower distortion by using a separating function intrinsically given to the human auditory organ. That is, the signal processing system of the present embodiment can reduce distortion while maintaining performance of signal separation. There is thus provided a signal processing system capable of imparting localization to a plurality of signal components contained in an input signal with smaller distortion, the localization being differentiated from signal component to component.

Moreover, the signal processing system described above may be implemented by a computer operated by a program.

Several embodiments have been described hereinabove, and examples of the present invention will be listed below:

The 1st embodiment of the present invention is characterized in that a signal processing system comprising a rendering section for receiving first and second input signals, and localizing the first input signal based on rendering information.

Furthermore, the 2nd embodiment of the present invention is characterized in that, in the above-mentioned embodiment, said rendering section localizes the second input signal at a position different from that of the first input signal.

Furthermore, the 3rd embodiment of the present invention is characterized in that, in the above-mentioned embodiment, the signal processing system further comprising an enhancement processing section for receiving a signal containing a plurality of signals, and enhancing a specific one of said plurality of signals to obtain said first input signal.

Furthermore, the 4th embodiment of the present invention is characterized in that, in the above-mentioned embodiment, said enhancement processing section enhances a specific signal in signals other than said specific signal to obtain said second input signal.

Furthermore, the 5th embodiment of the present invention is characterized in that, in the above-mentioned embodiment, said first input signal is a signal in which a desired signal is enhanced.

Furthermore, the 6th embodiment of the present invention is characterized in that, in the above-mentioned embodiment, said second input signal is a signal in which a signal other than a desired signal is enhanced.

Furthermore, the 7th embodiment of the present invention is characterized in that, in the above-mentioned embodiment, said desired signal is voice.

Furthermore, the 8th embodiment of the present invention is characterized in that, in the above-mentioned embodiment, the signal other than said desired signal is noise.

Furthermore, the 9th embodiment of the present invention is characterized in that, in the above-mentioned embodiment, the signal processing system further comprising a microphone for capturing a signal in which said desired signal and the signal other than said desired signal are mixed together.

Furthermore, the 10th embodiment of the present invention is characterized in that, in the above-mentioned embodiment, the signal processing system comprising: a plurality of said microphones; and a member for blocking between each pair of said plurality of microphones.

Furthermore, the 11th embodiment of the present invention is characterized in that, in the above-mentioned embodiment, the plurality of microphones are provided on different surfaces of a housing.

Furthermore the 12th embodiment of the present invention is characterized in that a signal processing apparatus comprising a rendering section for receiving first and second input signals, and localizing the first input signal based on rendering information.

Furthermore, the 13th embodiment of the present invention is characterized in that, in the above-mentioned embodiment, said rendering section localizes the second input signal at a position different from that of the first input signal.

Furthermore, the 14th embodiment of the present invention is characterized in that, in the above-mentioned embodiment, said first input signal is a signal in which a desired signal is enhanced.

Furthermore, the 15th embodiment of the present invention is characterized in that, in the above-mentioned embodiment, said second input signal is a signal in which a signal other than a desired signal is enhanced.

Furthermore, the 16th embodiment of the present invention is characterized in that, in the above-mentioned embodiment, said desired signal is voice.

Furthermore, the 17th embodiment of the present invention is characterized in that, in the above-mentioned embodiment, the signal other than said desired signal is noise.

Furthermore, the 18th embodiment of the present invention is characterized in that, in the above-mentioned embodiment, a signal processing apparatus further comprising a microphone for capturing a signal in which said desired signal and the signal other than said desired signal are mixed together.

Furthermore, the 19th embodiment of the present invention is characterized in that, in the above-mentioned embodiment, a signal processing apparatus comprising: a plurality of said microphones; and a member for blocking between each pair of said plurality of microphones.

Furthermore, the 20th embodiment of the present invention is characterized in that, in the above-mentioned embodiment, said plurality of microphones are provided on different surfaces of a housing.

Furthermore, the 21st embodiment of the present invention is characterized in that a signal processing method comprising: a receiving step of receiving first and second input signals; and a rendering step of localizing the first input signal based on rendering information.

Furthermore, the 22nd embodiment of the present invention is characterized in that, in the above-mentioned embodiment, in said rendering step, the second input signal is localized at a position different from that of the first input signal.

Furthermore, the 23rd embodiment of the present invention is characterized in that, in the above-mentioned embodiment, the signal processing method further comprising: a receiving step of receiving a signal containing a plurality of signals; and an enhancement processing step of enhancing a specific one of said plurality of signals to obtain said first input signal.

Furthermore, the 24th embodiment of the present invention is characterized in that, in the above-mentioned embodiment, in said enhancement processing step, a specific signal in signals other than said specific signal is enhanced to obtain said second input signal.

Furthermore, the 25th embodiment of the present invention is characterized in that, in the above-mentioned embodiment, said first input signal is a signal in which a desired signal is enhanced.

Furthermore, the 26th embodiment of the present invention is characterized in that, in the above-mentioned embodiment, said second input signal is a signal in which a signal other than a desired signal is enhanced.

Furthermore, the 27th embodiment of the present invention is characterized in that, in the above-mentioned embodiment, said desired signal is voice.

Furthermore, the 28th embodiment of the present invention is characterized in that, in the above-mentioned embodiment, the signal other than said desired signal is noise.

Furthermore, the 29th embodiment of the present invention is characterized in that, in the above-mentioned embodiment, the signal processing method further comprising a signal capturing step of capturing a signal in which said desired signal and the signal other than said desired signal are mixed together.

Furthermore, the 30th embodiment of the present invention is characterized in that a signal processing program causing a computer to execute: receiving processing of receiving first and second input signals; and rendering processing of localizing the first input signal based on rendering information.

Furthermore, the 31st embodiment of the present invention is characterized in that, in the above-mentioned embodiment, in said rendering processing, the second input signal is localized at a position different from that of the first input signal.

Furthermore, the 32nd embodiment of the present invention is characterized in that, in the above-mentioned embodiment, the signal processing program causing a computer to execute: receiving processing of receiving a signal containing a plurality of signals; and enhancement processing of enhancing a specific one of said plurality of signals to obtain said first input signal.

Furthermore, the 33rd embodiment of the present invention is characterized in that, in the above-mentioned embodiment, in said enhancement processing, a specific signal in signals other than said specific signal is enhanced to obtain said second input signal.

Furthermore, the 34th embodiment of the present invention is characterized in that, in the above-mentioned embodiment, said first input signal is a signal in which a desired signal is enhanced.

Furthermore, the 35th embodiment of the present invention is characterized in that, in the above-mentioned embodiment, said second input signal is a signal in which a signal other than a desired signal is enhanced.

Furthermore, the 36th embodiment of the present invention is characterized in that, in the above-mentioned embodiment, said desired signal is voice.

Furthermore, the 37th embodiment of the present invention is characterized in that, in the above-mentioned embodiment, the signal other than said desired signal is noise.

Furthermore, the 38th embodiment of the present invention is characterized in that, in the above-mentioned embodiment, the signal processing program causing a computer to execute: signal capturing processing of capturing a signal in which said desired signal and the signal other than said desired signal are mixed together.

Above, while the present invention has been described with respect to the preferred embodiments and examples, the present invention is not always limited to the above-mentioned embodiment and examples, and alterations to, variations of, and equivalent to these embodiments and the examples can be implemented without departing from the spirit and scope of the present invention.

This application is based upon and claims the benefit of priority from Japanese patent application No. 2007-271963, filed on Oct. 19, 2007, the disclosure of which is incorporated herein in its entirety by reference.

APPLICABILITY IN INDUSTRY

The present invention may be applied to an apparatus for signal processing or a program for implementing signal processing in a computer.

The invention claimed is:

1. A signal processing system comprising:

a first enhancement section configured to receive a first signal comprising a first plurality of mixed signal components, enhance a first component in the first plurality of mixed signal components, generate a first input signal comprising the enhanced first component, and output the first input signal;

a second enhancement section configured to receive a second signal comprising a second plurality of mixed signal components, enhance a second component in the second plurality of mixed signal components, generate a second input signal comprising the enhanced second component, and output the second input signal, wherein the second component is different from the first component;

a rendering section comprising a memory, said rendering section configured to receive said first and said second input signals and rendering information for operating localization of said first and second input signals, and localize said second input signal at a position different from that of said first input signal, wherein the first input signal is localized in a frontal spatial region, and the second input signal is localized in a rear spatial region based on a mixing of the rendered first and second input signals;

and a speaker associated with each of the first and second input signals configured to output the rendered first input signal and the second input signal, wherein said first input signal is a signal in which a desired signal is enhanced, and said second input signal is a signal in which a signal other than said desired signal is enhanced, wherein said desired signal is voice, and the signal other than said desired signal is noise.

2. The signal processing system according to claim 1, wherein said first input signal is a signal in which a desired signal is enhanced and said second input signal is a signal in which a signal other than a desired signal is enhanced, the signal processing system, further comprising a microphone for capturing a signal in which said desired signal and the signal other than said desired signal are mixed together.

3. A signal processing method comprising:

receiving a first signal comprising a first plurality of mixed signal components, enhancing a first component in the first plurality of mixed signal components, generating a first input signal comprising the enhanced first component, and outputting the first input signal;

receiving a second signal comprising a second plurality of mixed signal components, enhancing a second component in the second plurality of mixed signal components, generating a second input signal comprising the enhanced second component, and outputting the second input signal, wherein the second component is different from the first component;

receiving said first and said second input signals and rendering information for operating localization of said first and said second input signals, and localizing said second input signal at a position different from that of said first input signal, wherein the first input signal is localized in a frontal spatial region, and the second input signal is localized in a rear spatial region based on a mixing of the rendered first and second input signals;

and outputting the rendered first input signal and the second input signal by a speaker associated with each of the first and second input signals, wherein said first input signal is a signal in which a desired signal is enhanced, and said second input signal is a signal in which a signal other than said desired signal is enhanced, and wherein said desired signal is voice, and the signal other than said desired signal is noise.

4. The signal processing method according to claim 3, wherein said first input signal is a signal in which a desired signal is enhanced and said second input signal is a signal in which a signal other than a desired signal is enhanced, further comprising:

capturing a signal in which said desired signal and the signal other than said desired signal are mixed together.

5. A non-transitory computer readable storage medium storing computer instructions for causing a computer to execute the instructions, said instructions causing said computer to perform operations comprising:

receiving a first signal comprising a first plurality of mixed signal components, enhancing a first component in the first plurality of mixed signal components, generating a first input signal comprising the enhanced first component, and outputting the first input signal;

receiving a second signal comprising a second plurality of mixed signal components, enhancing a second component in the second plurality of mixed signal components, generating a second input signal comprising the enhanced second component, and outputting the second input signal, wherein the second component is different from the first component; and receiving said first and said second input signals and rendering information for operating localization of said first and said second input signals, and localizing said second input signal at a position different from that of said first input signal, wherein the first input signal is localized in a frontal spatial region, and the second input signal is localized in a rear spatial region based on a mixing of the rendered first and second input signals;

and outputting the rendered first input signal and the second input signal by a speaker associated with each of the first and second input signals, wherein said first input signal is a signal in which a desired signal is enhanced, and said second input signal is a signal in which a signal other than said desired signal is enhanced, and wherein said desired signal is voice, and the signal other than said desired signal is noise.

* * * * *